United States Patent
Azuma et al.

(10) Patent No.: US 6,839,457 B1
(45) Date of Patent: Jan. 4, 2005

(54) BONE MEASURING METHOD

(75) Inventors: Yoshiaki Azuma, Tokyo (JP);
Yoshifumi Harada, Tokyo (JP);
Norihiro Yamada, Tokyo (JP);
Tsutomu Maeda, Tokyo (JP);
Tomohiro Ohta, Tokyo (JP)

(73) Assignee: Teijin Limited, Osaka (JP)

( * ) Notice: Subject to any disclaimer, the term of this patent is extended or adjusted under 35 U.S.C. 154(b) by 512 days.

(21) Appl. No.: 09/744,814

(22) PCT Filed: Jun. 2, 2000

(86) PCT No.: PCT/JP00/03603

§ 371 (c)(1),
(2), (4) Date: Jan. 30, 2001

(87) PCT Pub. No.: WO00/74567

PCT Pub. Date: Dec. 14, 2000

(30) Foreign Application Priority Data

Jun. 3, 1999 (JP) .......................................... 11-156500

(51) Int. Cl.⁷ ................................................ G06K 9/00
(52) U.S. Cl. ....................... 382/131; 382/237; 382/298; 382/154; 382/173; 382/130; 382/199; 382/286; 600/407; 128/922
(58) Field of Search ................................. 382/128, 130, 382/131, 132, 199, 203, 209, 237, 258, 266, 285, 298, 286; 600/407; 645/424; 345/423; 128/922; 250/455.11; 356/39; 377/13

(56) References Cited

U.S. PATENT DOCUMENTS

| | | | | |
|---|---|---|---|---|
| 4,710,876 A | * | 12/1987 | Cline et al. ................. | 345/423 |
| 4,743,259 A | * | 5/1988 | Bolander et al. ........... | 128/898 |
| 5,835,619 A | | 11/1998 | Morimoto et al. | |
| 6,083,162 A | * | 7/2000 | Vining ........................ | 600/407 |
| 6,084,593 A | * | 7/2000 | Gibson ....................... | 345/426 |
| 6,112,109 A | * | 8/2000 | D'Urso ....................... | 600/407 |
| 6,115,048 A | * | 9/2000 | Cline et al. ................. | 345/424 |
| 6,430,427 B1 | * | 8/2002 | Lee et al. ................... | 600/407 |
| 6,591,004 B1 | * | 7/2003 | VanEssen et al. ........... | 382/154 |

* cited by examiner

Primary Examiner—Timothy M. Johnson
Assistant Examiner—Barry Choobin
(74) Attorney, Agent, or Firm—Rader, Fishman & Grauer PLLC

(57) ABSTRACT

This invention relates to a bone measurement method for measuring a bone shape, structure and architecture on the basis of the tomographic images of a test bone or joint, in more detail, to a bone measurement method characterized by having a template image extraction step for obtaining a wholly continued template image of a bone inner portion surrounded by a cortical bone from the binary image of a test bone cross section, and separating a cortical bone and a cancellous bone by the product of said template image and said binary image, as a bone measurement method which enables the automatic, high-speed and repeatable separation of a cortical bone and a cancellous bone on the basis of the binary image of a test bone or joint cross section and by which a separated three-dimensional image of the cortical bone portion and the cancellous bone portion is obtained as the bases for a non-invasive analyses of three-dimensional bone structure, bone strength, and the like.

12 Claims, 25 Drawing Sheets

<5A>

<5B>

<5C>

<5D>

<5E>

<5F>

<5G>
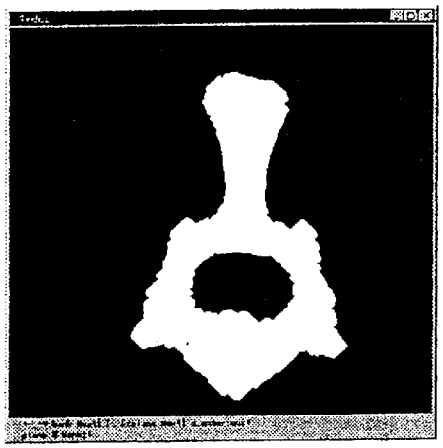
<5H>
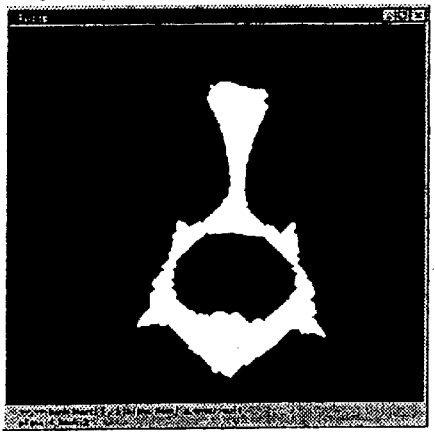
<5I>
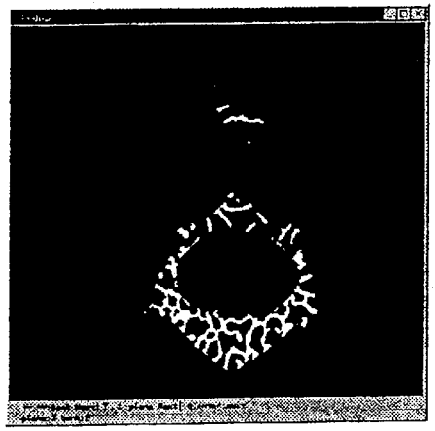
<5J>
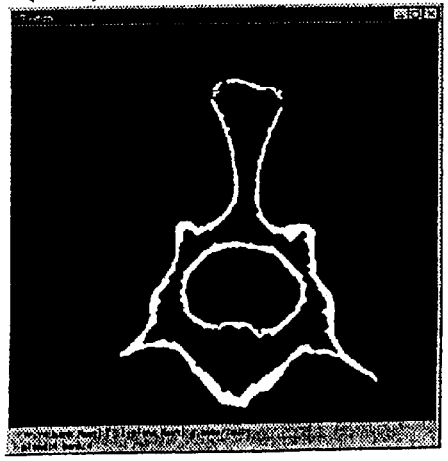
<5K>

< 6A >

< 6B >

< 8A >

< 8B >

//BONE MEASURING METHOD

TECHNICAL FIELD

The present invention relates to a bone measurement method for measuring a bone shape, structure and architecture on the tomographic images of a test bone or joint, in more detail, to a bone measurement method for separating a cancellous bone and a cortical bone on the basis of the binary images of a test bone or joint cross section, enabling the automatic, high-speed and repeatable separation of the cortical bone and the cancellous bone, and giving the separated three-dimensional images of the cortical bone portion and the cancellous bone portion as the bases for the non-invasive analyses of three-dimensional bone structure, bone strength, and the like. Further, the present invention relates to a bone measurement method which comprises applying a method (advanced Marching Cube method) for defining the boundary surface of an object to a separated cross section (hereinafter referred to as "connected surface") in the separated three-dimensional images of the cortical bone and the cancellous bone on the bases of the binary images of the test bone or joint cross section, enables the efficient, automatic, high-speed and repeatable definition of the boundary surface, and gives the three-dimensional image of a boundary surface site as an index for non-invasively analyzing the three-dimensional bone structure, the bone strength, and the like.

BACKGROUND ART

It has been pointed out as a means for evaluating the bone strength to evaluate the bone structure. The many types of bone of a skeleton consist of cortical bones and cancellous bones, which are considered to have different bone structures and different roles, respectively. When a large load is applied to a bone, the bone is estimated to structurally act so that the cortical bone portion resists to the large load and so that the cancellous bone portion absorbs the impact.

Thereby, for the evaluation of the structure of the bone, the cortical bone portion and the cancellous bone portion must be separately and quantitatively evaluated. The cortical bones are mostly structurally continued to the cancellous bones, and it is difficult to specify the boundaries between both the bones. Hence, a bone measurement method, which enables the separation of the cortical bone from the cancellous bone in strictly good repeatability, is demanded.

On the other hand, the following bone measurement method, which enables the automatic separation of the cortical bone portion and the cancellous bone portion, has been proposed in JP-A No. 9-294740 (hereinafter, JP-A presents Japanese Unexamined Patent Publication). The method comprises separating the cortical bone portion from the cancellous bone portion by the use of the thinned images of the bone portions on the basis of the binary image of the tomographic image of a test bone, concretely a method which comprises thinning the bone portions, estimating the average bone width of the cortical bone from the outside bone portion of the thinned image, and then expanding the thinned image on the estimated value to determine the cortical bone portion.

However, the method includes a case that the cortical bone portion or the cancerous bone portion is divided, whereby a problem may be caused, when a plurality of test bones are compared with each other by the method. The present invention was achieved with respect to the problem, and the first purpose of the invention is to provide a bone measurement method which enables the stable separation of a cortical bone and a cancellous bone, even when a test bone, that is, a testee, is different, the non-invasive construction of the three-dimensional structure of bone, particularly the accurate three-dimensional evaluation of the bone, and further the high-speed and automatic separation of the cortical bone and the cancellous bone in good repeatability. Further, the second purpose of the invention is to provide a bone measurement method; which enables the stable production of the boundary surface between the cortical bone and the cancellous bone even when the testee is different, the non-invasive definition of the boundary of the bone, and the high-speed and automatic measurement of characteristics (the number, area, peripheral length and circular degree of the boundary surface) for quantitatively evaluating the characteristics of the boundary surface in good repeatability.

DISCLOSURE OF THE INVENTION

The above-mentioned first purpose is achieved by the following present invention. Namely, the present invention is a bone measurement method for separating a cortical bone and a cancerous bone on the basis of the binary image of a test bone or joint cross section, characterized by having a template image-extracting step for measuring the singly connected template image of a bone inner portion surrounded by the cortical bone from the binary image, and separating the cortical bone and the cancellous bone by the product of the template image and the binary image.

The present invention was achieved by finding out that the template image enables the extraction of the whole bone portion and thereby the separation of the cortical bone from the cancerous bone in good repeatability and further that the extraction step enables high speed processing to achieve the purpose, because of being composed of a highly simple algorithm.

In the present invention, the separated images of the cortical bone and the cancellous bone can simply be changed into the separated gray-value images by the product of the obtained binary separated images and the non-binary gray-scale images.

Further, three dimensional images are obtained at a high speed by making separated cortical bone portion images and separated cancellous bone portion images from the plural continuous tomographic images of the test bone at a prescribed distance and then stacking the separated cortical bone portion images and the separated cancellous bone portion images to form the three-dimensional separated bone images, respectively. When gray-value separated images, that is, grayscale separated images, are used as the separated images, the separated cortical bone portion three-dimensional image and the separated cancellous bone portion three-dimensional image are obtained.

Thus, the present invention enables the more accurate evaluation of the three-dimensional bone-related information than those by other methods, because the separated cortical bone portion three-dimensional image and the separated cancellous bone portion three-dimensional image can non-invasively and automatically be extracted at a high speed in good repeatability.

Further, in the present invention, a method (advanced Marching Cubes method Japanese patent No. 0279856) for defining the boundary surface of an object is applied to the cut and separated surface (hereinafter referred to as "boundary surface") on the three dimensional images obtained by stacking the separated cortical bone portion images and the separated cancellous bone portion images in the slicing directions (cross-section direction), respectively, thus using the image-processing means for continuously defining triangles on the boundary surface.

Usually, the Marching Cubes method usually defines one or more polygonal surfaces on a boundary surface between a background and an object in a binary three-dimensional object image, and is now applied to the definition of the boundary surface between the cortical bone and the cancellous bone. By the method, the boundary surface defined by the triangles can be defined.

And, the number of the boundary surfaces is measured by a processing means for retrieving the connected states of the vertex coordinates of the triangles and then counting up the number of the labels of the boundary surfaces from the connected states.

The bone measurement method is also characterized in that the area of the boundary surface is obtained by multiplying the areas of the triangles for each label.

The bone measurement method is also characterized in that the peripheral length is obtained by multiplying the lengths of the outermost sides of the triangles for each label.

The bone measurement method is also characterized in that the circular degree (complexity) is obtained by quantifying the complexity of the boundary surface from the areas and peripheral lengths of the triangles for each label, wherein a perfect circle is defined as 1.

Thus, by the present invention, the boundary surface images between the separated cortical bone and the separated cancellous bone can non-invasively and automatically be extracted at a high speed and in good repeatability, thereby enabling the more accurate evaluation and measurement of the three-dimensional bone-related information.

Hereinafter, the details of the present invention are explained.

Figure 1:
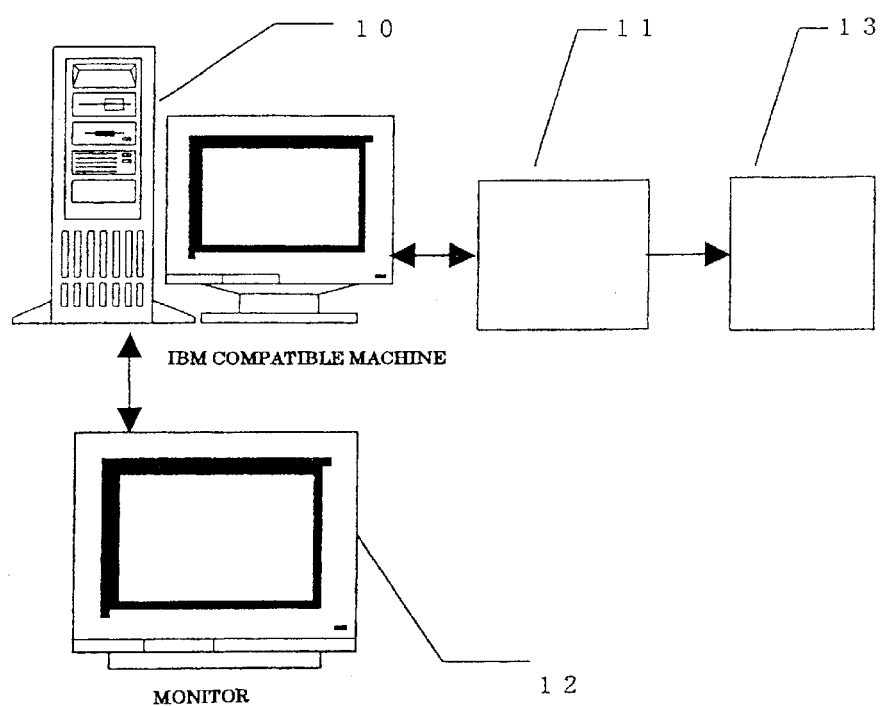
FIG. 1 is an explanatory drawing constituting an apparatus example for carrying out the present invention.

The marks in the drawings indicate as follows, respectively.
10. an image processor
11. a personal computer
12. an image-processing board
13. a hard disk
20. a bone portion
21. a cortical bone portion
22. a cancerous bone portion
23. a medullary cavity portion (space portion)
24. a spinal cord cavity portion (cave portion)
25. a background portion
30. an element
31. a node
32. a side

BEST MODE FOR CARRYING OUT THE INVENTION

The present invention will sequentially be explained together with the form of the execution of the invention on the basis of an example applied to the lumber vertebra of a rat as follows. An example for the femur of a rat will also be described, and it will further be showed that the invention can also be applied to a long bone.

(1). Bone measurement method by which a cortical bone and a cancellous bone can be separated from each other The cross sections of a rat lumber vertebra as a test bone were scanned using a microfocused X-ray computed tomographic apparatus (hereinafter referred to as "$\mu$X-ray CT") having a focal size and a resolution sufficient for measuring the fine structures of the cancellous bone as a scanning means, similarly as the above-described JP-A No. 9-294740. An apparatus for generating two-dimensional information, such as a high resolution X-ray apparatus, a nuclear magnetic resonance imaging diagnostic apparatus (MRI) or a film scanner, may also be applied to the scanning of the test bone.

Figure 2:
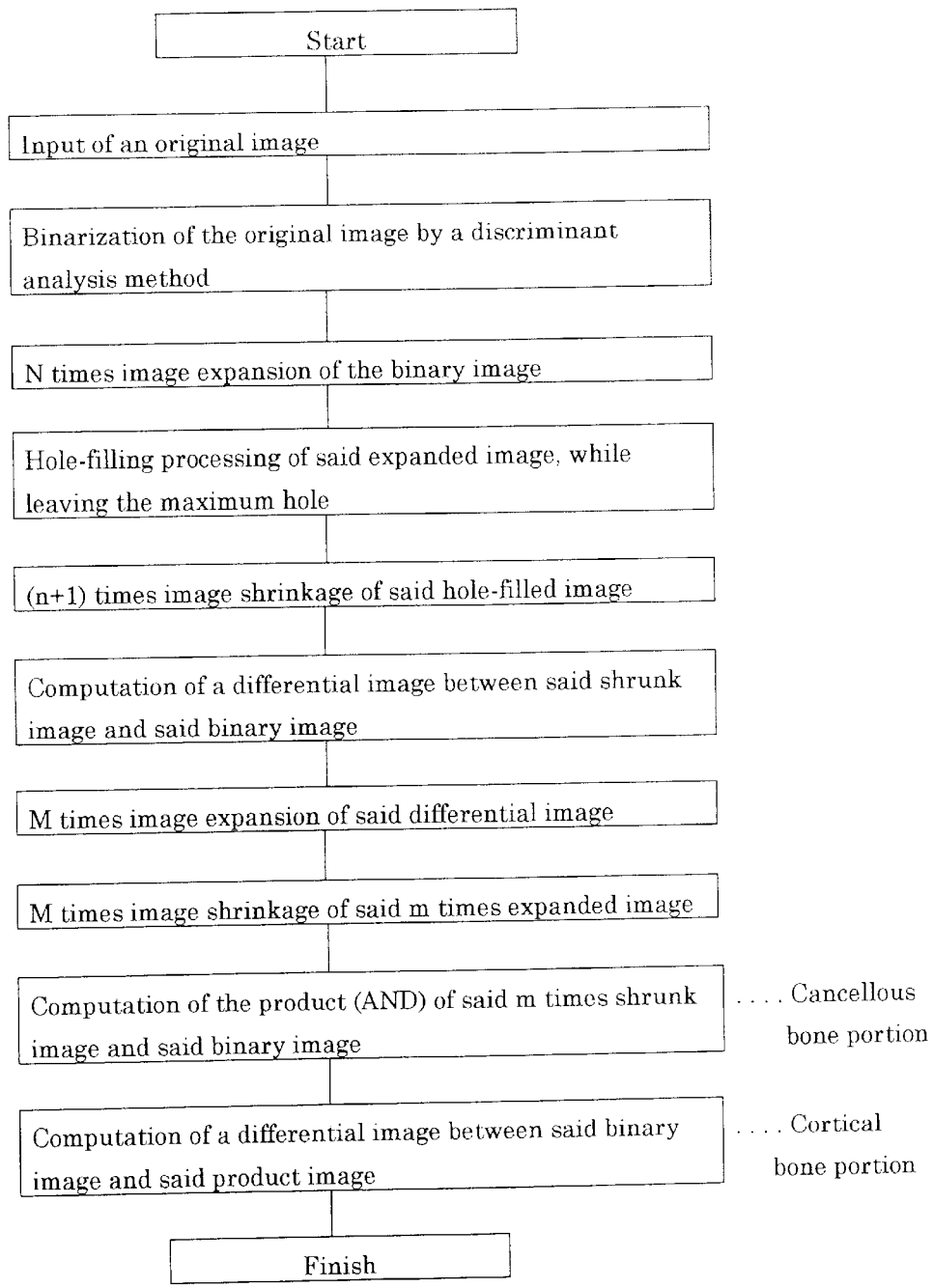
FIG. 2 is a flow chart of a separation processing means for separating a cortical bone and a cancellous bone.

And, the test bone image signals obtained by the scanning means were processed with the following image processor to carry out the bone measurement. As shown in FIG. 1, the image processor 10 of the present example was provided with an image-processing board 12 (Sharp Semiconductor Corp. GPB-K in the present example) exclusively used for processing images and with a mass storage hard disk 13 for memorizing images, and a personal computer 11 on which an external monitor 14 for displaying images was loaded was used. The image processor 10 stored the processing program of the flow chart shown in FIG. 2, and processed the test bone image signals obtained from the scanning means to automatically extract and separate the bone portion into the cortical portion and the cancellous bone portion as follows.

Prior to the processing, the continuous tomograms of the rat lumbar vertebra of the test bone were scanned using the $\mu$X-ray CT at a prescribed distance in the axial direction to obtain the image signals, similarly as the above-described JP-A No. 9-294740. It is preferable that the images have a space resolution in an extent (10 to 25 $\mu$m) sufficient for observing the trabecular bone. The $\mu$X-ray CT images used in the present example had a length of 512 pixels, a width of 512 pixels and a height (axial direction) of 30 slices (possible to the maximum of 512 slices), and were expressed in a size of about 20 $\mu$m to 25 $\mu$m per pixel of the cross section, at a slice distance of about 20 $\mu$m and at a luminance value CT (also called a concentration value) of $2^8$ gradations for each pixel.

Figure 3:
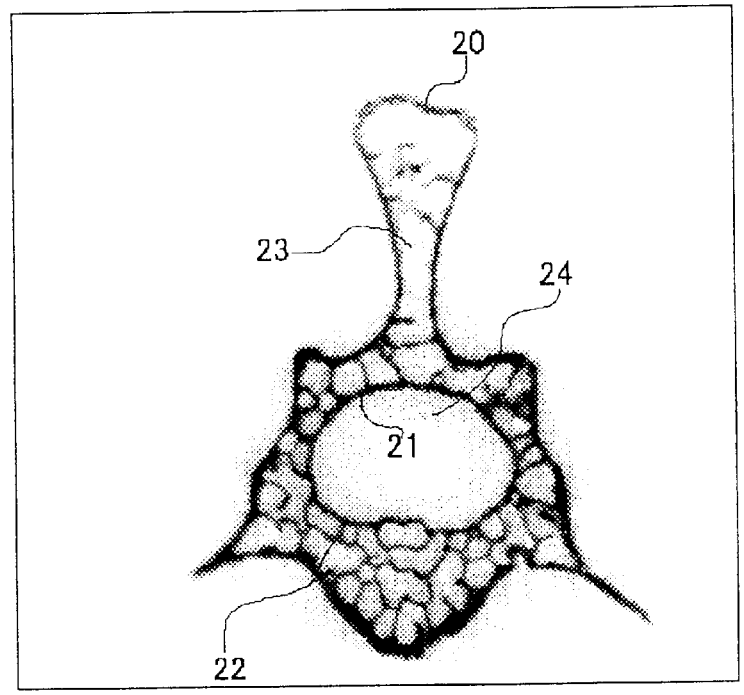
FIG. 3 is an original image of the rat lumbar vertebra cross section.

FIG. 3 is a representative example among the luminance value-displayed grayscale images (hereinafter referred to as "original image") of the cross sections of the rat test bone lumbar vertebra, obtained using the $\mu$X-ray CT. In FIG. 3, 20 is a bone portion, and 21 is its cortical bone portion which comprises an outside portion appearing on the outside contour and an inside portion appearing on the inside contour. The net-like intraosseous linear portion surrounded by the cortical portion 21 is a cancellous bone portion 22. 23 and 24 in FIG. 3 are a spinal cord cavity portion (hereinafter referred to as space portion) and a spinal cord cavity portion (hereinafter referred to as "cave portion"), respectively, and the outside of the bone portion 20 is a background portion 25. In the original image of the grayscale image in FIG. 3, the boundaries of the cortical bone portion 21, the cancerous bone portion 22 and the space portion 23 are obscure, and the mutual separation of the portions is difficult in such the states.

The original image is taken in the image processor 10 in the step 1. In the binarization step of the step 2, the original image taken thus is converted into a binary image by a discriminating analysis method as follows similarly as the above-described Japanese Unexamined Patent Publication.

The discriminating analysis method can be used for determining a binary threshold, when a concentration difference in a group is small and when a concentration deviation between groups is large, and is suitable for the bone measurement which is the target of the present invention.

In the discriminating analysis method, it is assumed that the group of luminance values is divided into two classes with a threshold in the histogram of the luminance values of images, and the threshold is determined so that the distribution ratio ($f_0$) of the equation 1 is maximized using the interclass distribution of the below-described equation 2 and the intraclass distribution of the below-described equation 3, followed by binarizing the images with the determined threshold.

$$f_0 = \delta b^2 / \delta w^2 \qquad \text{Equation 1}$$

Wherein, $f_0$: distribution ratio $\delta b^2$: interclass distribution $\delta w^2$: intraclass distribution $$\delta b^2 = \omega_1 \omega_2 (m_1 - m_2)^2 \qquad \text{Equation 2}$$

Wherein, $\omega_1$: the number of pixels in class 1

$\omega_2$: the number of pixels in class 2

$m_1$: the average luminance value of class 1

$m_2$: the average luminance value of class 2

$$\delta w^2 = \omega_1 \delta_1^2 + \omega_2 \delta_2^2 \qquad \text{Equation 3}$$

Wherein, $\delta_1$: the distribution of the luminance values of the pixels of class 1

$\delta_2$: the distribution of the luminance values of the pixels of class 2

Figure 4:
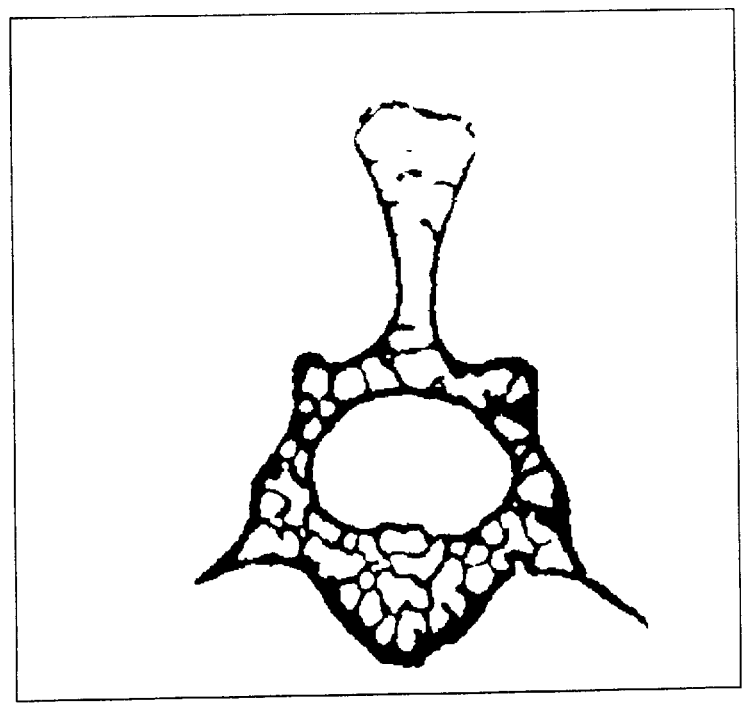
FIG. 4 is a binary image of the rat lumbar vertebra cross section.

In the present example, a threshold was determined by preparing the histogram of the luminance values of the original image, selecting the candidates of the threshold from the histogram, and then changing the candidates to give the optimal value. The numerical characters of 1 were assigned to the larger luminance values than the threshold, and the numerical characters of 0 were assigned to the smaller luminance values than the threshold to binarize the luminance values, whereby the binary image was obtained. FIG. 4 shows a binary image (hereinafter referred to as "binary original image") obtained by binarizing the original image of FIG. 3. From FIG. 4, it is found that the distinctions of the space portion 23 from the cortical portion 21 and the cancellous portion 22 are clear.

And, in the present example, an inside region in which the cancerous bone 22 exists and which is surrounded by the outside and inside cortical bone portions 21 is extracted as a template image from the binary original image at the following step for extracting the template image on the basis of the eight-neighbor known as a binary image-processing method.

Figure 5:
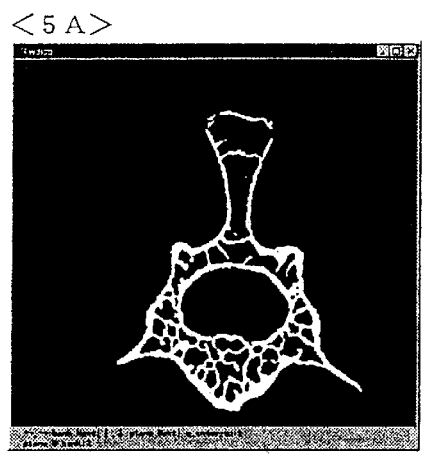
FIG. 5 is an explanatory drawing of a method for separating the cortical bone and the cancellous bone.
Figure 5:
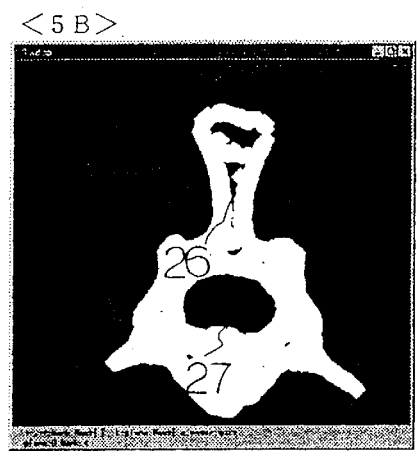
Figure 5:
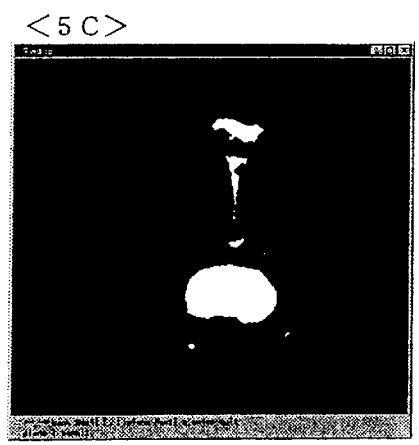
Figure 5:
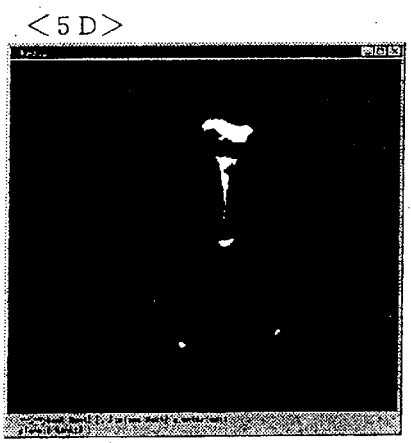
Figure 5:
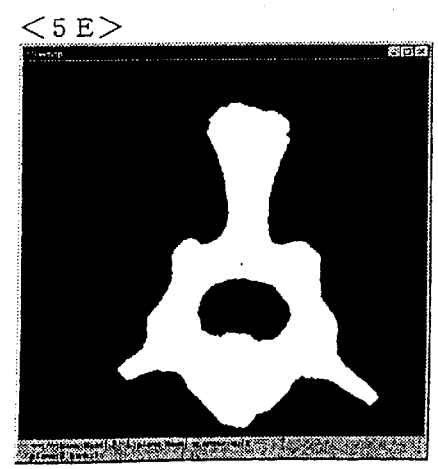
Figure 5:
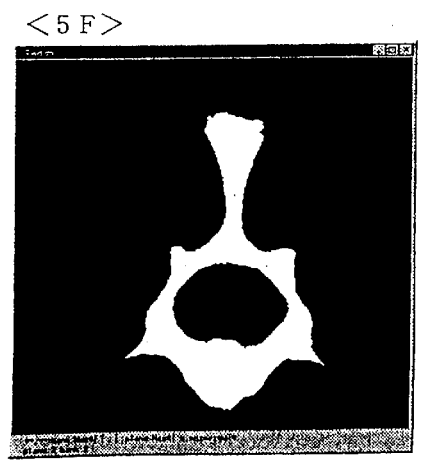

First, since the binary original image usually has noises such as isolated points, the following noise processing is carried out in the smoothing processing step of step 3. In the present example, isolated points at places near to eight-neighbors were deleted from the binary original image as the noise processing. The method for deleting the isolated points at the places near to the eight-neighbors is a processing method comprising noticing a certain pixel, scanning pixels placed in the neighboring eight directions and then assigning 0 to the noticed pixel, only when all the luminance values of the pixels are 0. The noise-processed image is shown in FIG. 5A.

Then, a connection processing for virtually connecting the divided portions of the cortical portion 22 or the like, divided by blood vessels or the like, is carried out. The connection processing was carried out by applying an expansion processing for the one layer thickening of the boundary points of the image N times. It is necessary that the expansion processing is carried out times sufficient for connecting the divided portions, and in the present example, the N was 10 due to the distances of the divided portions. The processed image is shown in FIG. 5B. It can be found from FIG. 5B that hole portions 26 corresponding to the space portions 23 of the inner region surrounded by the cortical bone portion 21 and a background hole portion 27 corresponding to the cave portion 24 surrounded by the inside cortical bone portion 21 are left in the bone portion image.

By the way, for the determination of the inner bone image region where the cancellous bone portion 22 exists, namely a template image, it is necessary that all the hole portions 26 of the inner region are filled to form a hole portion-free singly connected region. It is thereby needed for the image processing that only the hole portions 26 in the inner region are filled and deleted to leave the background hole portion 27 as such. When the image processing is carried out in such a way as not leaving the background hole portion 27, the image processing can also sufficiently be applied to a long bone such as a femur.

The hole-filling processing was performed at the hole-filling step of the step 5 as follows. The expanded image obtained at the above-described expanding step was first inverted to obtain the reverse image, which is shown in FIG. 5C. Since the background hole portion 27 to be left among the white portions corresponding to the hole portions 26 and the background hole portion 27 has the maximum area in the reverse image, the areas of the white portions were computed, and a processing for removing the background portions excluding the white portion having the maximum area was carried out to delete the central oval white portion corresponding to the background hole portion 27 in the Figure. Although needed for the test bone lumbar vertebra having the cave portion 24 in the present example, the background portion-removing processing is not necessary for a femur or the like which does not have such a cave portion, and may be omitted. The hole-filling image obtained by the processing is shown in FIG. 5D. It can be found from the FIG. 5D that the hole-filling image has the white portions corresponding to all the holes 26 of the inner region. The sum (OR) image of the obtained hole-filling image of FIG. 5D and the expanded image of FIG. 5B obtained at the above-described expanding step was computed, and is shown in FIG. 5E. It is found from FIG. 5E that the expanded and connected image which did not have the hole portion 26 and in which the whole region of the bone portion 20 surrounded by the singly connected cortical bone portion 21 was completely continued was obtained.

By the way, the expanded and connected image is the image obtained by carrying out the expansion processing N times, ten times in the present example, as described above, and has the size of the expanded binary original image. The expanded and connected image was hence shrunk to a size corresponding to the binary original image at the shrinking step of the step 6. In the present example, the shrinking processing for removing the boundary points of the image and reducing one layer was carried out (N+1) times, concretely 11 times. In order to return the size of the expanded image to the size of the original image, the shrinking processing is generally carried out the same times as those of the expanding processing. However, these processings have not only the simple expanding and shrinking functions but also the prescribed functions such as the smoothing function and the hole-filling function, as well known. Since it is important to extract the inner region surrounded by the cortical bone portion 21 as the template image, the shrinking processing was carried out more times by once than those of the expanding processing so as not to leave the outside of the cortical bone portion 21, in the present example. Thereby, the stable inner region could be extracted without being affected by the shape of the cortical bone portion 21. The image obtained at the shrinking step is shown in FIG. 5F. The connected and shrunk image obtained from the above processing is the perfectly continued image which contains the cortical bone portion 21 of the contour portion and does not have a hole in the bone portion 20 surrounded by the cortical bone portion.

On the other hand, the template image for extracting the cancellous bone portion 22 is the inner wholly continuous image of the bone portion 20 not containing the cortical bone portion 21. Therefore, the step 7 and the subsequent cortical bone portion-removing steps are carried out for removing the cortical bone portion 21. Namely, the smoothened binary original image (FIG. 5A) obtained in the step 3 is subtracted from the connected shrunk image obtained at the step 6 to obtain the differential image. The differential image is displayed in FIG. 5G. The obtained differential image is a bone space portion image obtained by removing the cortical bone portion 21 and the cancerous bone portion 22 from the wholly connected image of the bone portion 20.

On the other view, it is found that the bone space portion image is a template image which is the image of the inner region obtained by removing the cortical bone portion 21 from the bone portion 20 surrounded by the cortical bone portion 21, namely the image of the region where the cancellous bone portion exists, when the net portion of the cancellous bone portion 22 in the bone space portion image is filled. Then, the following step-removing step of the step 8 for removing the spaces of the cancellous bone portion 22 was carried out for obtaining the template image. Concretely, the following processing was performed for connecting the spaces left by removing the cancellous bone portion 22 in FIG. 5G, thereby obtaining one wholly continued region. In the connection processing, the above described image-expanding processing was applied M times to connect the spaces in the FIG. 5G. The obtained image is shown in FIG. 5H. FIG. 5H shows the image of the wholly continued singly connected region in which the spaces were removed. The above-described image-shrinking processing was applied the same M times for returning the size to the original size. The obtained image is shown in FIG. 5I. FIG. 5I is the template image of the inner region image in which, to be detected the cancellous bone portion is surrounded by the cortical bone portion 2 existing. In the present example, M was 10 due to the widths of the spaces to be connected. Thus, the cancellous bone template image for detecting the cancellous bone portion 22 was obtained.

And, the product (AND) image of the template image for the cancellous bone and the above-described smoothened binary original image shown in FIG. 5A was obtained at the cancellous bone portion detection step of the step 10, whereby the binary cancellous bone image could be detected. The result is displayed in FIG. 5J. The binary cancellous bone image was then subtracted from the above-described smoothened binary original image displayed in FIG. 5A to obtain the differential image, whereby the binary cortical bone image could be detected. The obtained image is shown in FIG. 5K. Both the obtained images were good.

As above, it is found by the present invention that the cortical bone portion and the cancellous bone portion could automatically be separated by the simple processings.

Figure 6:
FIG. 6 is grayscale images of the cortical bone and the cancellous bone, after separated.
Figure 6:
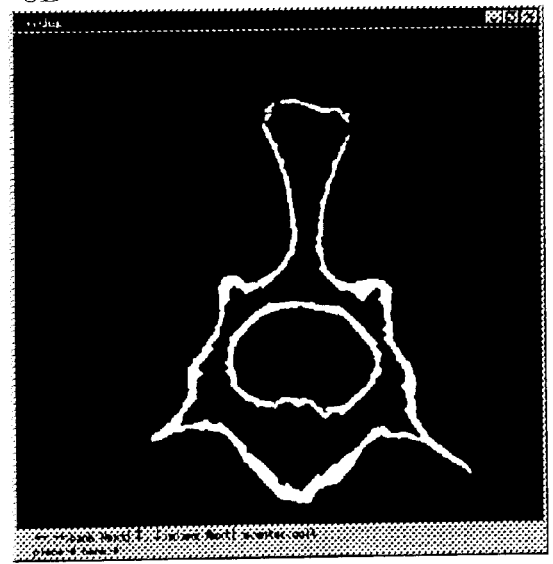

Semi-thresholded images which hold the luminance values of the inputted original image and in which the luminance values of the background regions are zero can also be obtained from the binary cortical bone image and the binary cancellous bone image obtained by the above-described method by simple processing. Concretely, the semi-thresholded images of the binary cortical bone image and the binary cancellous bone image could be obtained by forming images having the minimum luminance values from the original image of FIG. 3 and the images of the binary cortical bone portion and the cancerous bone portion, respectively. The results are shown in FIG. 6. FIG. 6A is the semi-thresholded image of the binary cortical bone portion, and FIG. 6B is the semi-thresholded image of the binary cancerous bone portion image.

Figure 7:
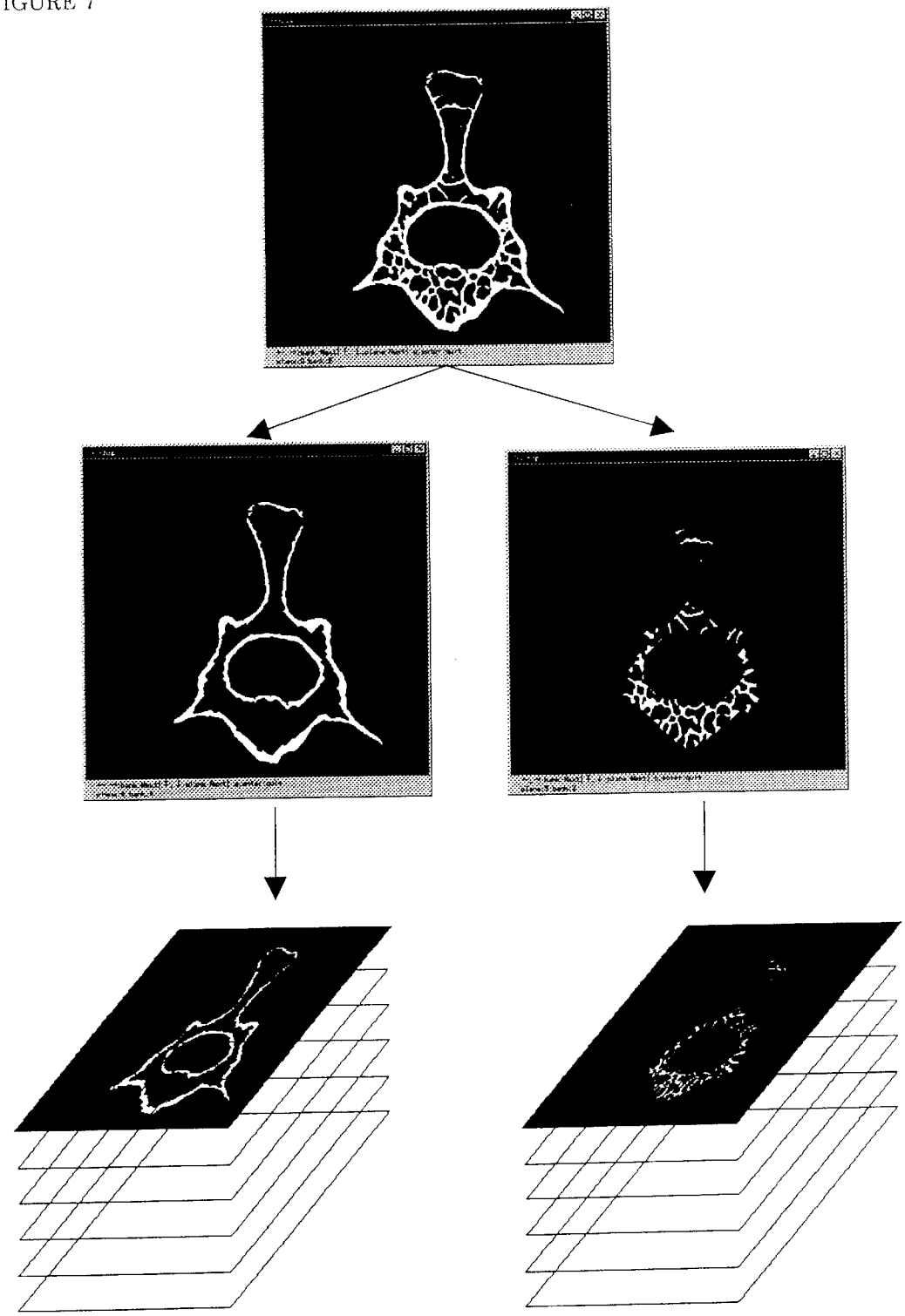
FIG. 7 is an explanatory drawing for explaining the production of three-dimensional images.
Figure 8:
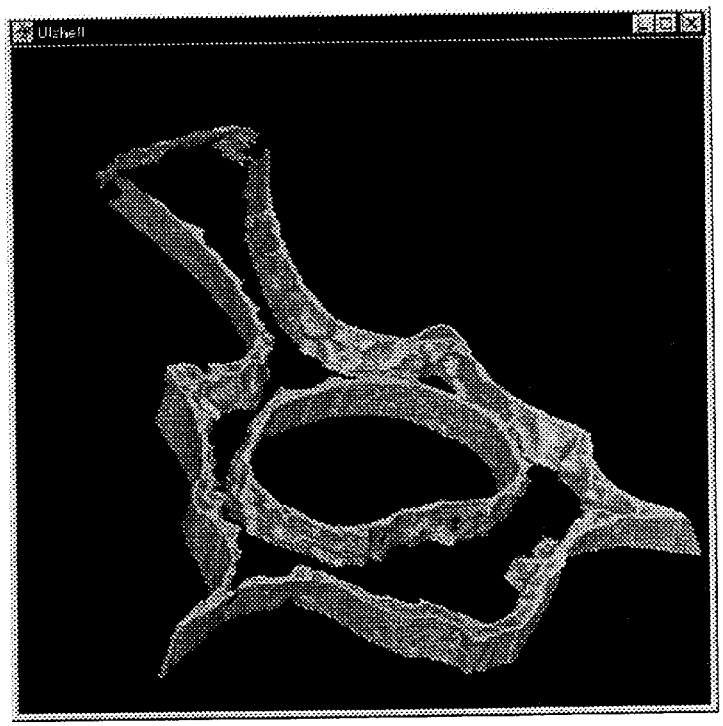
FIG. 8 is a drawing for showing the produced three-dimensional images of the cortical bone and the cancellous bone.
Figure 8:
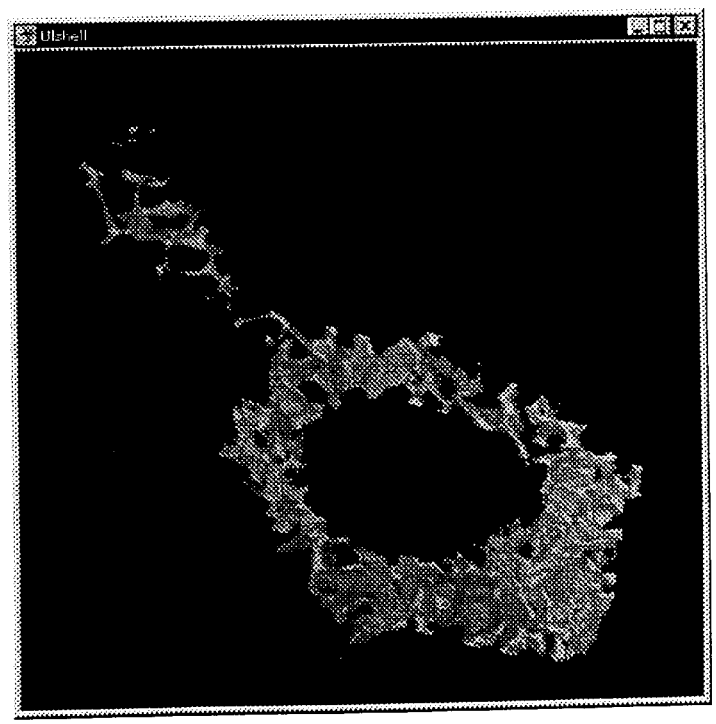

Further, as shown in FIG. 7, the three-dimensional images of the cortical bone portion and the cancerous bone portion could be obtained by processing continuous images obtained by scanning the bone in its axial direction at a prescribed slice distance by the above-described processing method and then stacking the obtained semi-thresholded image data of the cortical bone portions and the cancellous bone portions of FIG. 6 in the slice direction, respectively. The results are shown in FIG. 8. FIGS. 8A and 8B are the three-dimensional images of the cortical bone portion and the cancellous bone portion, respectively, and it is found that the highly good three-dimensional images were obtained.

(2) Method for producing boundary surfaces between a cortical bone and a cancellous bone and for quantitatively evaluating the characteristics of the boundary surfaces.

The cross sections of a rat lumber vertebra as a test bone were scanned using a microfocused X-ray computed tomography (hereinafter referred to as "$\mu$X-ray CT") having a focal size and a resolution sufficient for measuring the fine structures of the cancellous bone as a scanning means in the present example, similarly as the JP-A No. 9-294740. An apparatus for generating two-dimensional information, such as a high resolution X-ray apparatus, a nuclear magnetic resonance imaging diagnostic apparatus (MRI) or a film scanner may also be applied to the scanning of the test bone.

And, the image signals of the test bone, which are obtained by the scanning means, are processed by the following image processor to carry out the bone measurement. As shown in FIG. 1, the image processor 10 of the present example was provided with an image-processing board 12 (Sharp Semiconductor Corp. GPB-K in the present example) exclusively used for processing images and with a mass storage hard disk 13 for memorizing images, and a personal computer 11 on which an external monitor 14 for displaying images was loaded was used. The image processor 10 stores the processing program of the flow chart shown in FIG. 9, and automatically extracts and separates the bone portion into the cortical portion and the cancellous bone portion by the method described in the (1) of "Best Mode for Carrying Out the Invention".

First, the continuous tomograms of the rat lumbar vertebra of the test bone are scanned using the $\mu$X-ray CT at a prescribed distance in the axial direction and then input into the image processor 10 to obtain the images (hereinafter, referred to as "separation-processed images") in which the cortical bones and the cancellous bones were separated. It is preferable that the images have a space resolution in an extent (10 to 25 $\mu$m) sufficient for observing the bone trabecula. The $\mu$X-ray CT images used in the present example have a length of 512 pixels, a width of 512 pixels and a height (axial direction) of 200 slices (possible to the maximum of 512 slices), and are expressed in a size of about 20 to 25 $\mu$m per pixel of the cross section, at a slice distance of about 20 $\mu$m and at a gray-value CT (also called a concentration value) of $2^8$ gradations per pixel. The images are read into the image processor 10 at the step 1 for inputting the original image in FIG. 9. FIG. 10 is the original image of the rat lumbar vertebra.

Figure 9:
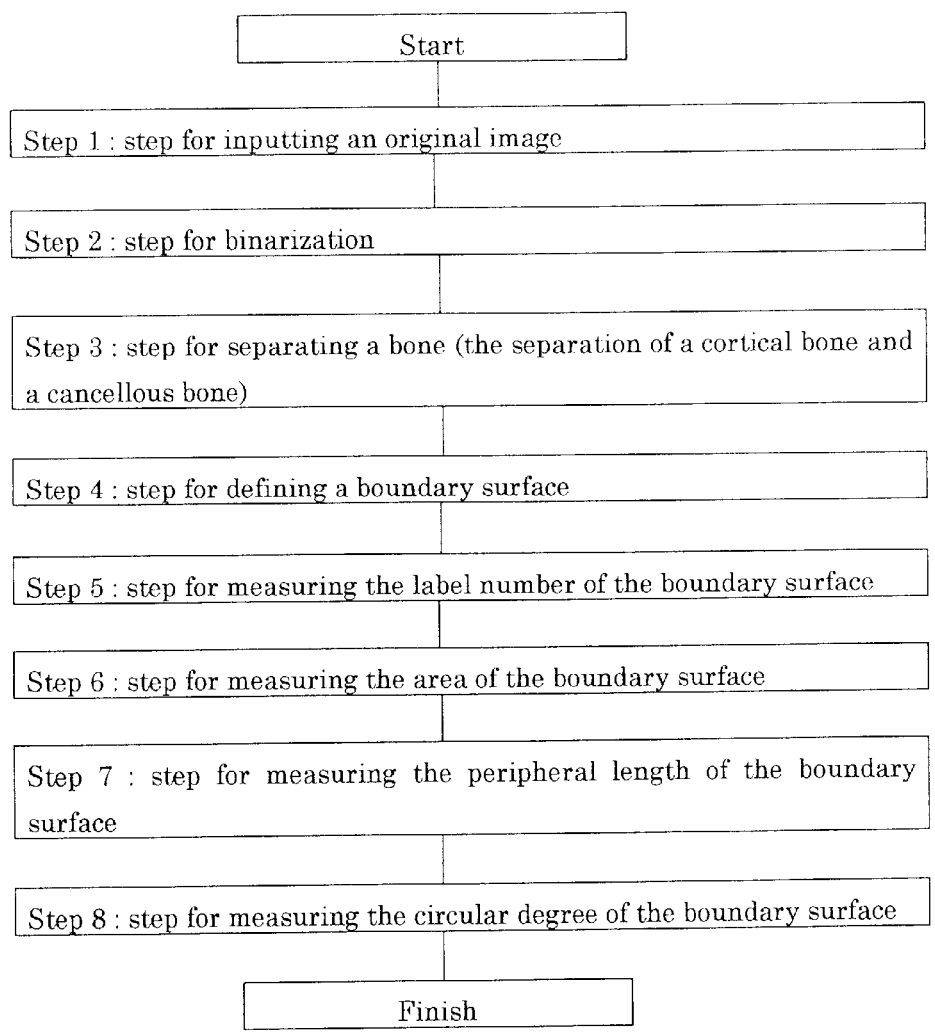
FIG. 9 is a whole flow chart for computing the characteristics of a boundary surface.
Figure 10:
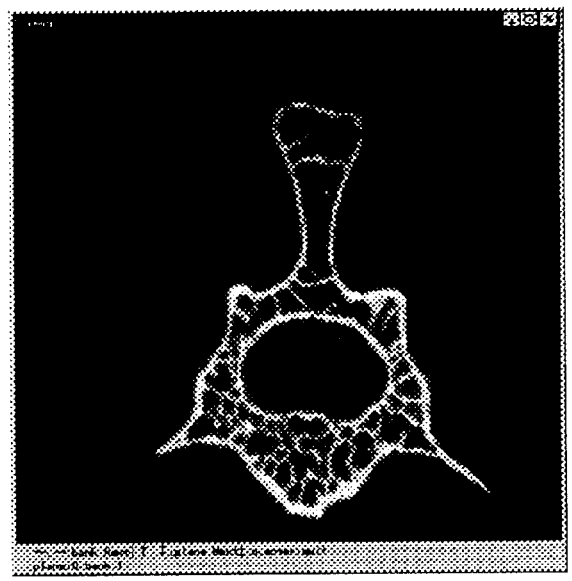
FIG. 10 is an original image of the rat lumbar vertebra cross section.

The binarization step of the step 2 in FIG. 9 is carried out. Therein, a discriminating analysis method is used as the binarization method.

Figure 11:
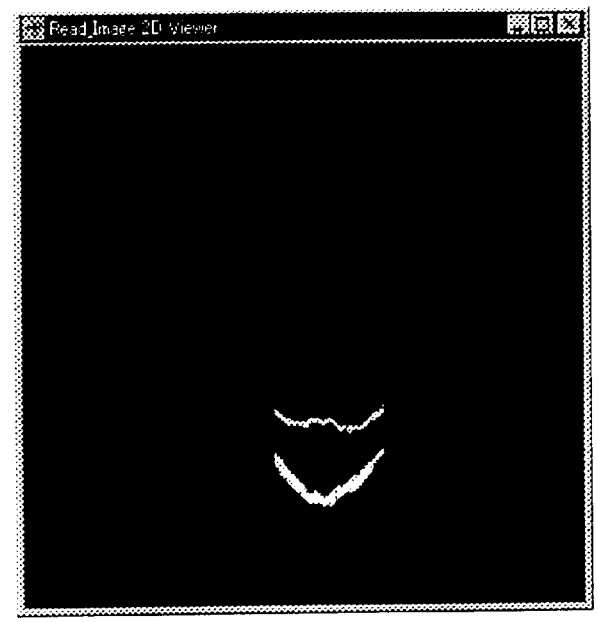
FIG. 11 is a binary image of the cortical bone in the rat lumber vertebra cross section.
Figure 12:
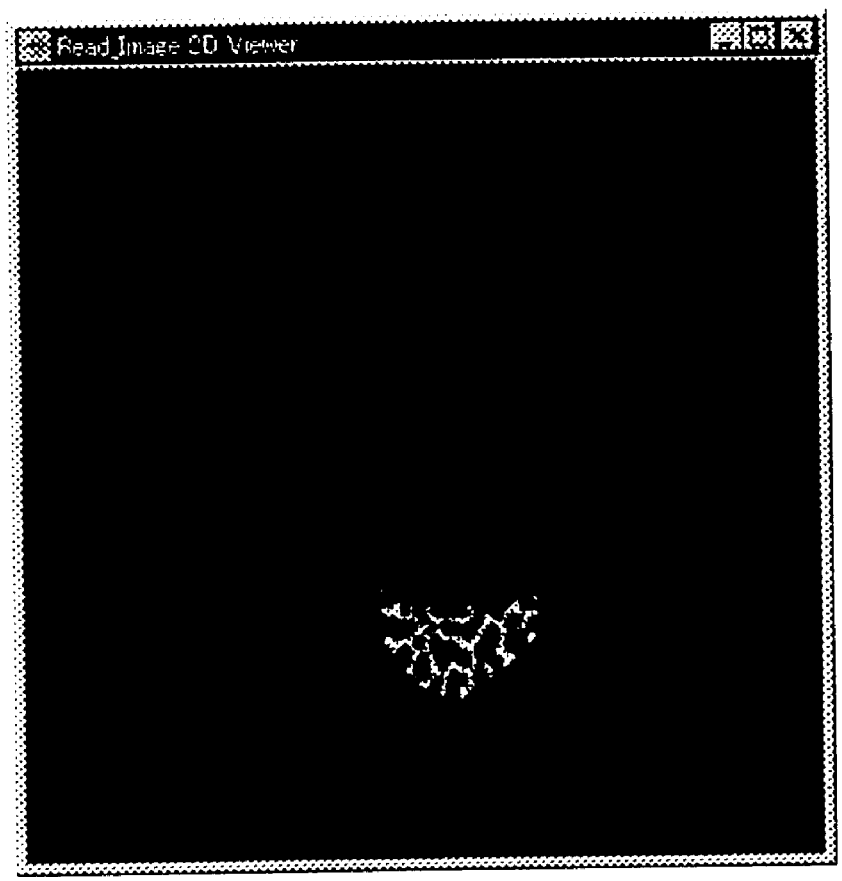
FIG. 12 is a binary image of the cancellous bone in the rat lumbar vertebra cross section.
Figure 13:
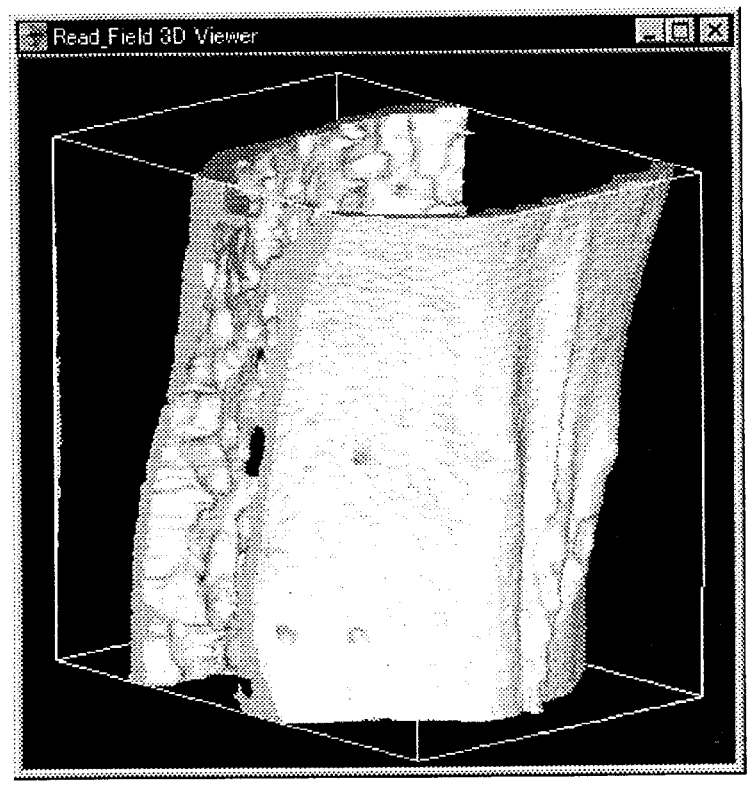
FIG. 13 is a three-dimensional visible image of the cortical bone of the rat lumbar vertebra.
Figure 14:
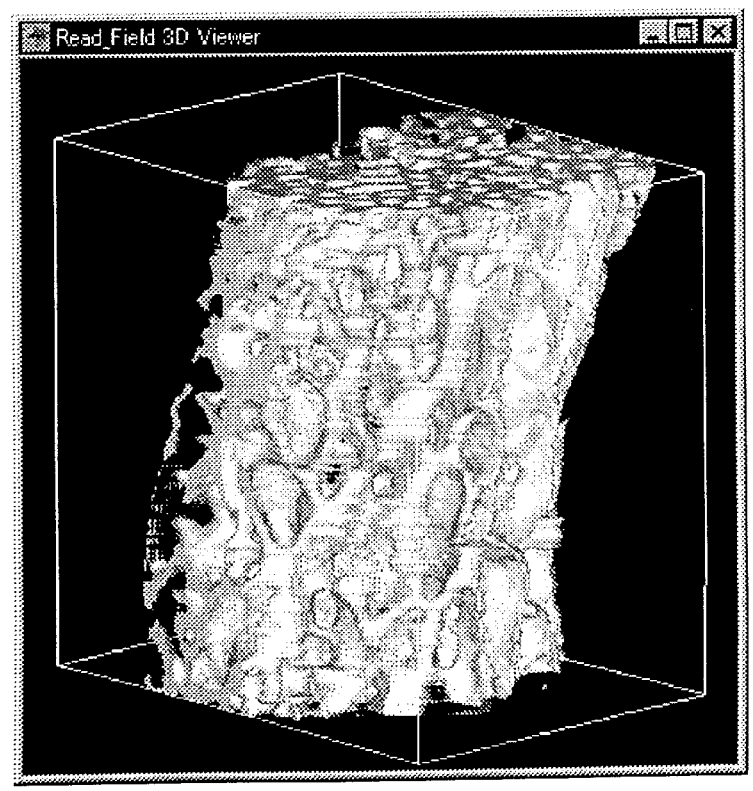
FIG. 14 is a three-dimensional visible image of the cancellous bone of the rat lumbar vertebra.
Figure 15:
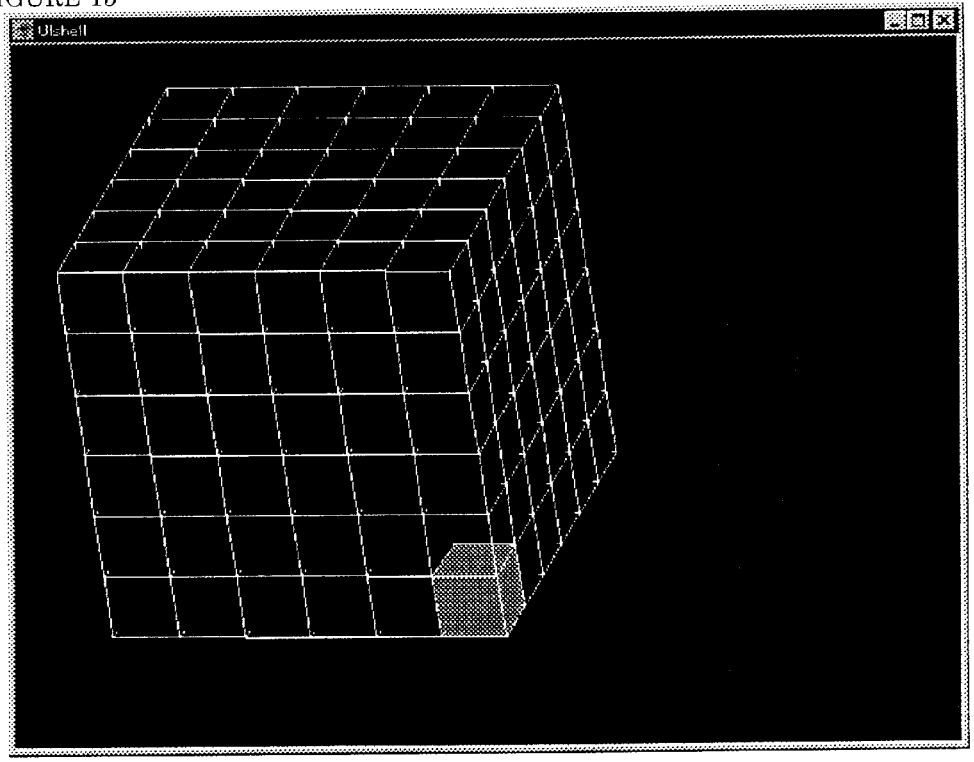
FIG. 15 is a drawing for explaining the definition of voxels.

The processing for separating the cortical bone (FIG. 11) and the cancellous bone (FIG. 12) is carried out plural times at the step 3 in FIG. 9, and the necessary number of the obtained images were stacked in a lattice-like form in the slice direction (cross-sectional direction). The representative examples are shown in FIG. 13 and FIG. 14. The cortical bone is shown in such a three-dimensional image as that of FIG. 13, and the cancerous bone is also shown in such a three-dimensional image as that of FIG. 14. The OR image of these images (FIG. 13 and FIG. 14) is the whole bone image. A voxel is obtained by thickening each pixel on a two-dimensional image as shown in FIG. 15.

Figure 16:
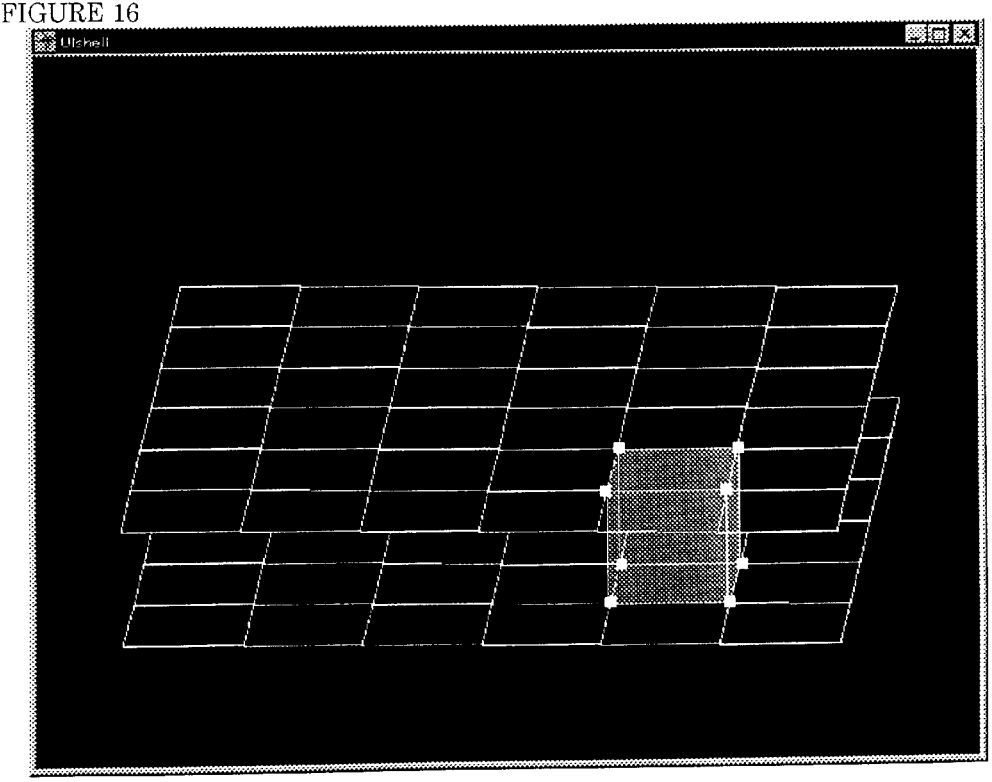
FIG. 16 is a drawing for explaining the definition of cubes.
Figure 17:
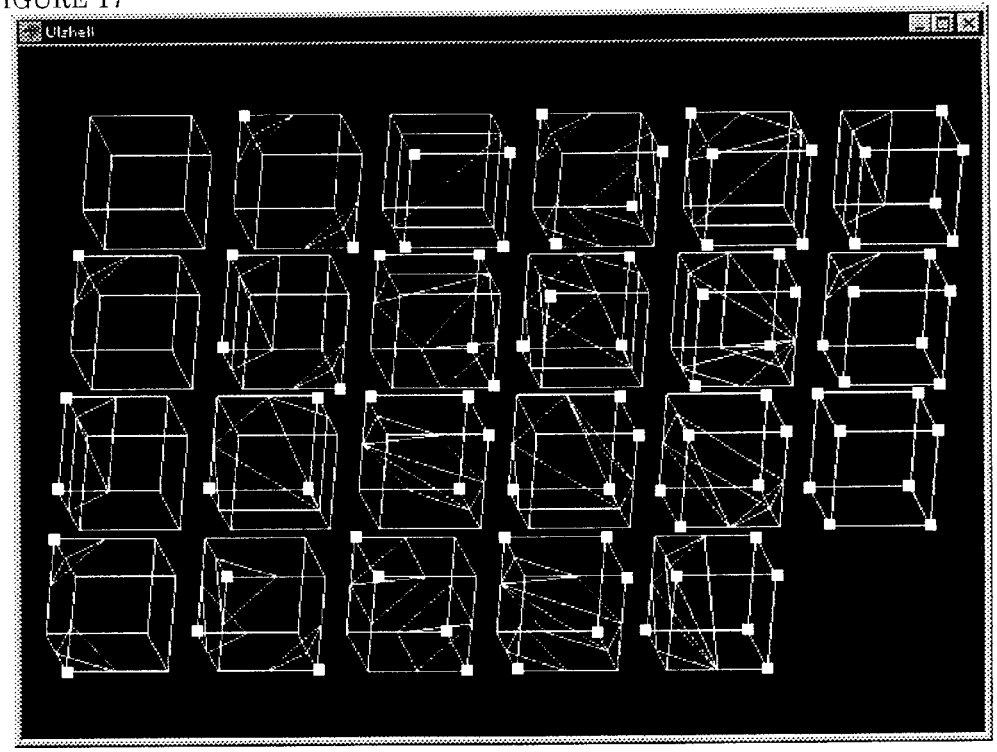
FIG. 17 is a drawing for showing the pattern of the advanced Marching Cubes method.

Here, it is general to use a Marching Cubes method for the general definition of the surface shape of an object. The Marching Cubes method is a method for estimating pixels for covering a voxel aggregate from the local arrangement of the voxel aggregate and then approximating the surfaces of the voxels to polygons (triangles in the present invention) to form the surface of the object. Concretely, as shown in FIG. 16, the surface shape of the object is confirmed by considering eight-neighbor voxels as the vertexes of a cube as shown in FIG. 16 and then measuring whether the vertexes (voxels) contain voxel values (pixel values) (1) or not (0). When the vertex contains the voxel value, the voxel value is 1 (570), and when the vertex does not contain the voxel value, the voxel value is 0 (nothing). Then, $2^8=256$ kinds of combinations are possible as the combinations of the vertexes 1 and 0, but when rotation and symmetry are considered, the combinations are 23 kinds in FIG. 17. Patch-labeled surfaces (triangles in the case of the present example) can be estimated for the boundary surfaces of the three-dimensional object by the present method.

A step (step 4 in FIG. 9) to which the Marching Cubes method is applied is shown as follows.

The treatments of the voxel values of the cortical bone (FIG. 13) and the cancellous bone (FIG. 14) are defined as follows as preconditions.

Definition formula 4: cortical bone portion→1

Definition formula 5: cancellous bone portion→2

Definition formula 6: background portion→0

The definition formula 4 defines that the voxel value of the cortical bone region is 1 in FIG. 13. The definition formula 5 defines that the voxel value of the cancellous bone region is 2 in FIG. 14. The definition formula 6 further defines that the voxel value of the background regions of FIG. 13 and FIG. 14 is 0.

Here, the estimation of the boundary surfaces between the cortical bone and the cancellous bone means that the voxel values on the explained cubes satisfy all of the following conditions.

Definition formula 7: the voxel values comprise both the voxel values of 1 and 0.

Definition formula 8: there is not the background value (0).

The definition formula 7 shows that both the regions of the cortical bone and the cancellous bone exist at the vertexes of an object cube, and means that there certainly exists a boundary surface. (0) means that a background does not exit at the vertexes of the object cube.

Figure 18:
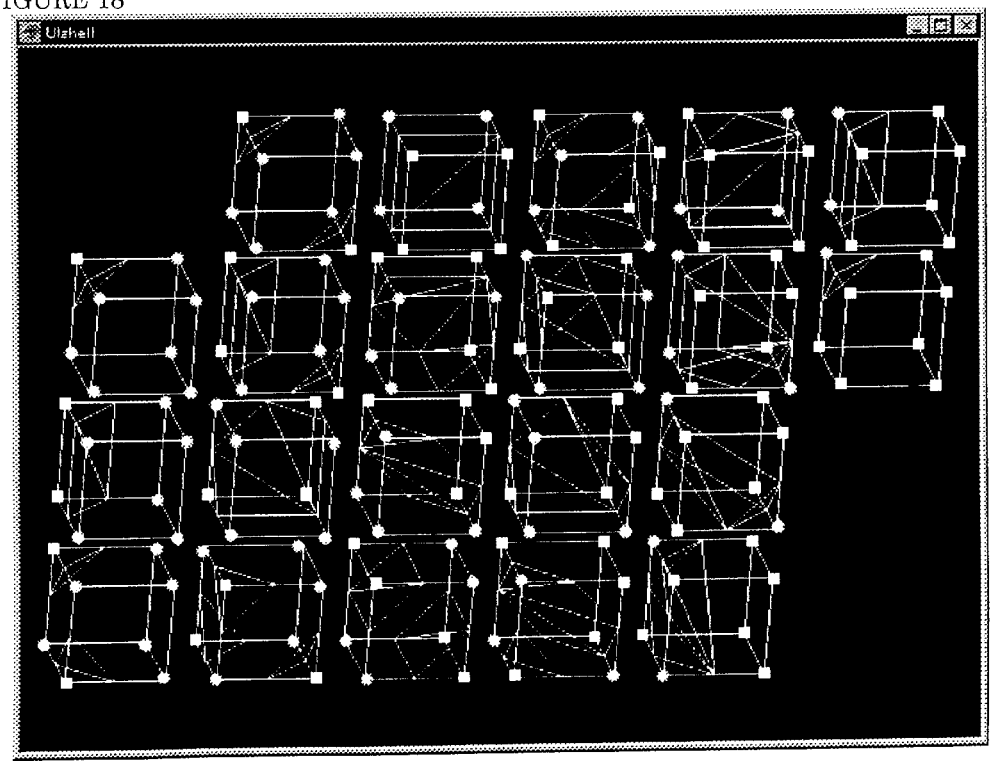
FIG. 18 is a drawing for showing the pattern of the boundary surface of the present case.
Figure 19:
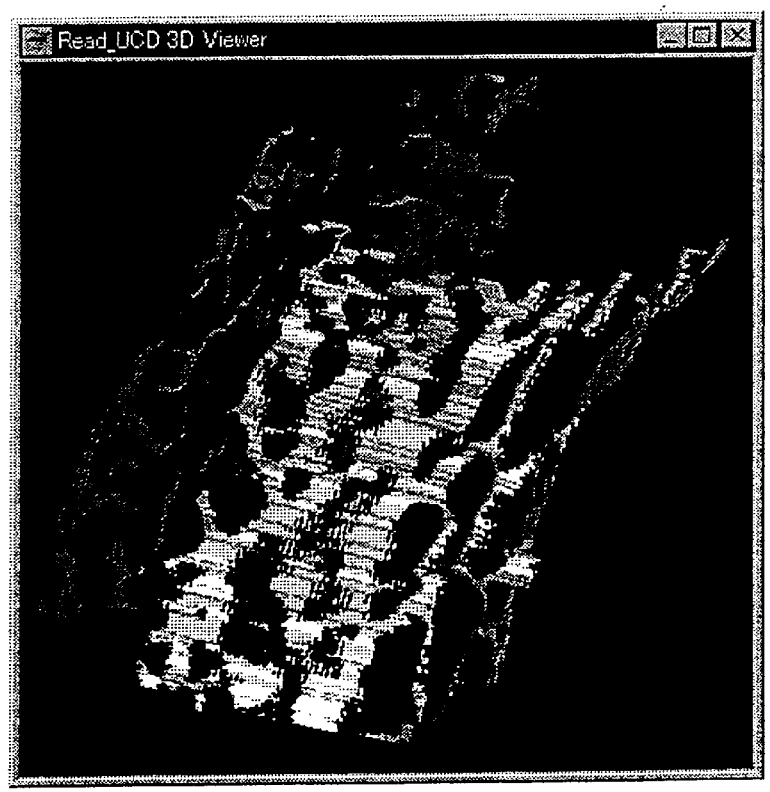
FIG. 19 is a drawing for showing boundary surfaces between the cortical bone and the cancerous bone of the rat lumbar vertebra.

When combinations satisfying both the conditions of the definition formulas 7,8 are considered and when rotation and symmetry are also considered, the patterns of the boundary cubes between the cortical bone and the cancellous bone are gathered into 23−2=21 kinds of the patterns. When the cortical bone portion and the cancellous bone portion are temporarily designated as (■) and (●), respectively, patterns as shown in FIG. 18 are obtained. When boundary surface shapes are formed by applying the method and visualized, an image such as the image in FIG. 19 can be obtained.

Figure 20:
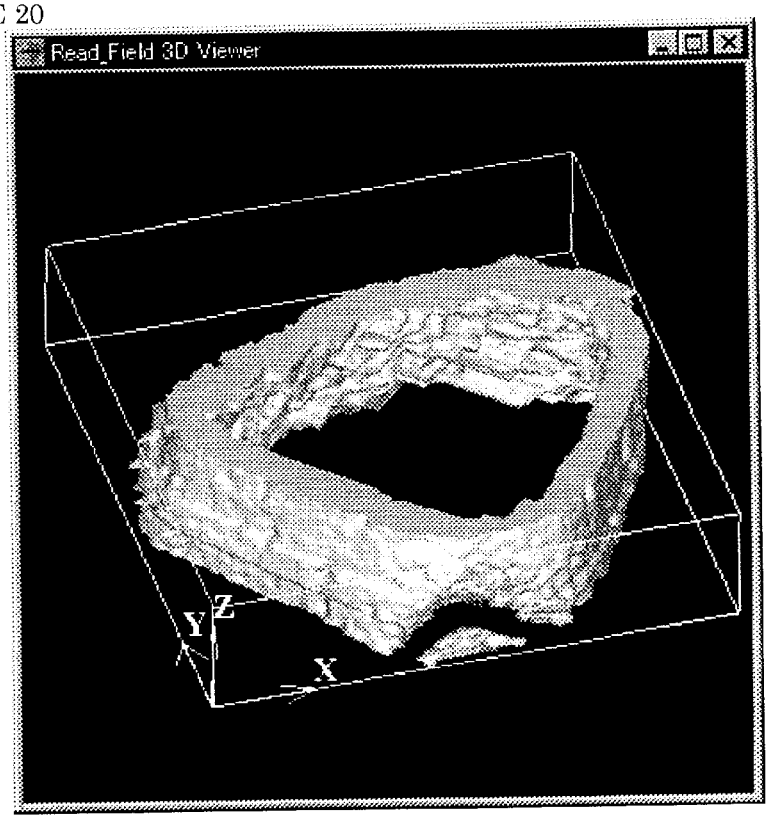
FIG. 20 is a three-dimensional visible image of the cortical bone of the rat femur.
Figure 21:
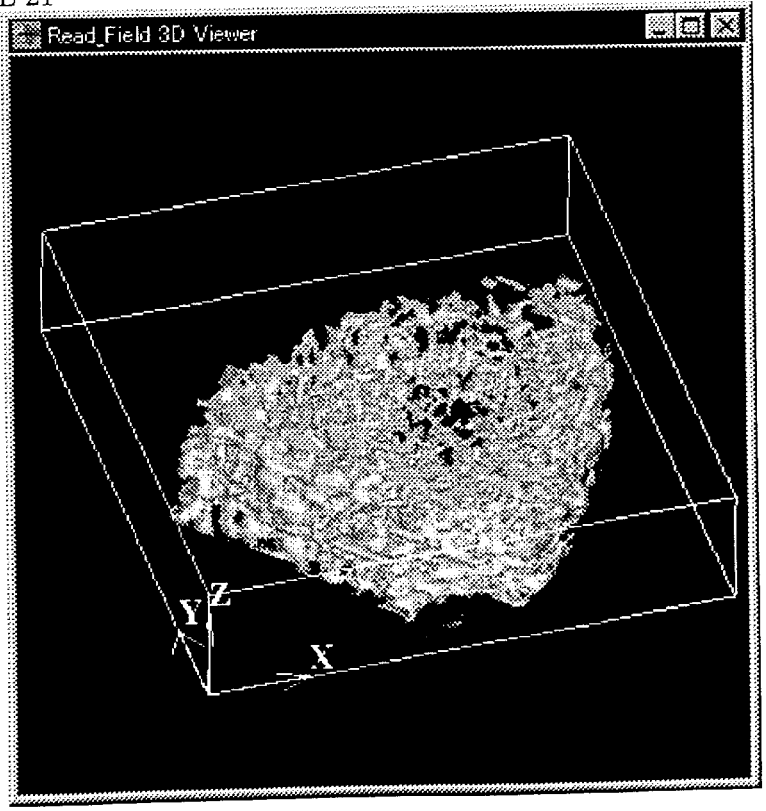
FIG. 21 is a three-dimensional visible image of the cancellous bone of the rat femur.
Figure 22:
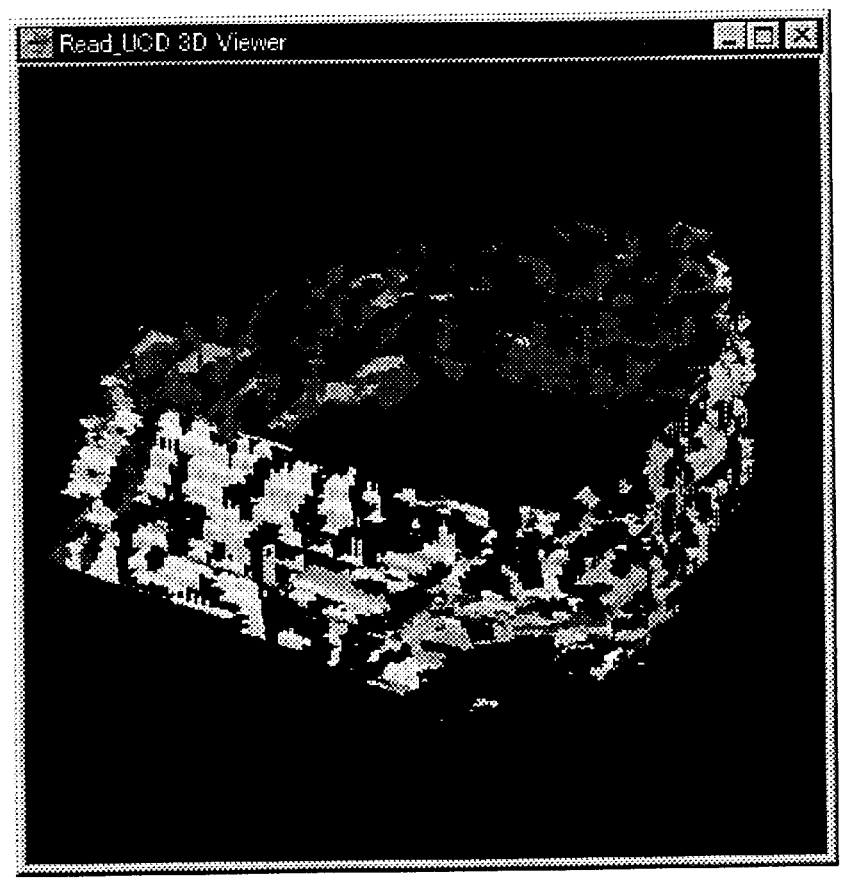
FIG. 22 is a drawing for showing boundary surfaces between the cortical bone and the cancellous bone of the rat femur.

Further, an application example to the rat femur is shown. Therein, the example shows that the method can generally be applied not only to the rat femur but also to long bones. The cortical bone and the cancellous bone of the rat femur are separated by the prescribed method and shown as three-dimensional images in FIG. 20 and FIG. 21. The connected surface shape of the femur is also shown in FIG. 22.

The obtained boundary surfaces are used to sequentially measure the label number, areas, peripheral lengths and circular degrees of the bone boundary surfaces at the steps 5, 6, 7 and 8 of the FIG. 9.

Figure 23:
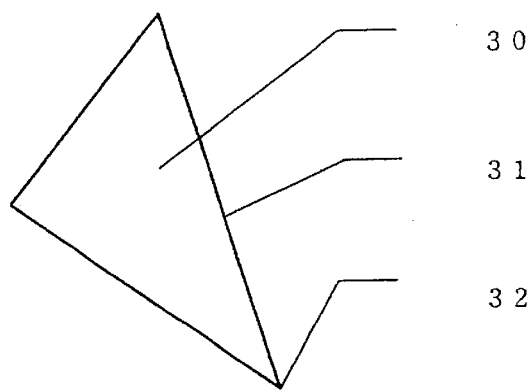
FIG. 23 is a drawing for explaining the terms of triangle elements.

Methods and procedures for measuring the shapes of the defined boundary surfaces between the cortical bone and the cancellous bone are shown as follows. The element 30, the node 31 and the side 32 of a triangle defined as a boundary surface are shown in FIG. 23.

Figure 24:
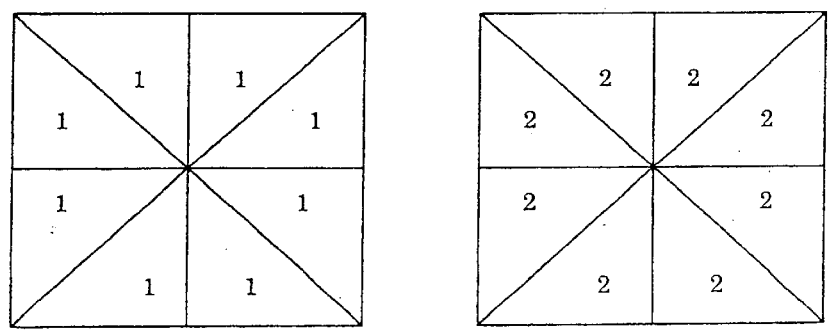
FIG. 24 is drawings for showing the definition of labeling.

First, the label number of the boundary surfaces is the number of the surfaces independently existing in a space. Concretely, when the objects shown in FIG. 24 exist, two surfaces of the left object and of the right object exist. The explained method for producing the boundary surfaces defines a triangular element for a unit cube but does not recognize the number of the surfaces in a wide area by the use of the image processor 10. The number of the bone boundary surfaces can be used as a basic unit on the measurements of the surfaces, when the sites of the boundary surfaces are quantified.

Figure 25:
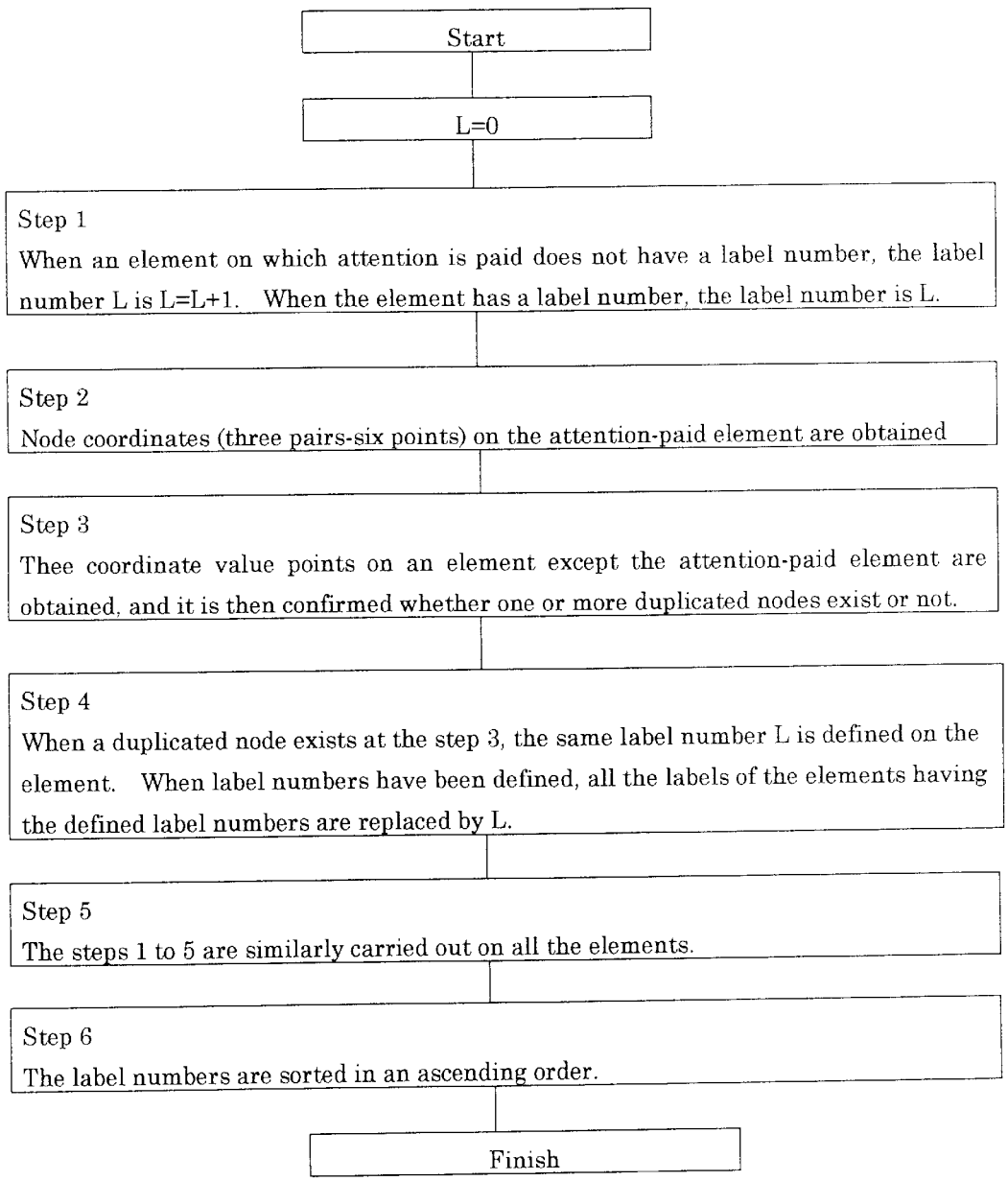
FIG. 25 is a flow chart for determining the number of boundary surfaces.

The measurement of the number (hereinafter referred to as "label number") of boundary surfaces is carried out by paying attention on the coordinate of a node on a surface existing in an element-like state, confirming whether one or more nodes having the same coordinate exist or not, then paying attention on the next node after the first processing, and thus repeating the processing for all the nodes. Concretely, the positions and number of labels on boundary surfaces are determined along the flow of FIG. 25. First, a label number-setting processing is carried out at the step 1 in FIG. 25. Attention is paid on an element, and a label number is set to the element. Therein, when the label number has not been defined, the label number is L (L=L+1), but, when the label number has been defined, the defined label number is L. Then, the three pair six points of the coordinate (X, Y, Z) of a node existing on the attention-paid element are obtained at the step 2 in FIG. 25. Further, the three points of the coordinate points (X, Y, Z) of the element except the attention-paid elements are obtained at the step 3 in FIG. 25. Then, it is confirmed on all the nodes whether one or more duplicated nodes exist or not. When a duplicated node exists at the step 3 of FIG. 25, the label number L is set to the element. When label numbers have been already defined, all the element labels, having the label numbers set temporarily, are replaced by L. The processing at the step 4 in FIG. 25 is applied to all the elements. After the processing at the step 4 in FIG. 25 is finished, the processing is returned to the step 1 in FIG. 25, and the processing at the step 1 to the processing at the step 4 are applied to the next other element label. After all the elements are processed by the method, the defined label numbers are subjected to an ascending sort at the step 6 of FIG. 6. The maximum value of the sorted label number is consequently the objective label number (the number of the boundary surfaces).

When the elements are extremely many in the processing, the processing at the step 3 needs a long time in some cases. In the cases, the trouble can be solved by comparing elements existing on the same slice as a cube having the attention-paid element with elements existing on cubes in three upper and lower slices without confirming the presence of duplicated nodes on all the nodes.

Then, the measurement of the areas of the boundary surfaces is carried out by totalizing the triangular element areas obtained by computing the hollowing equations.

$$s[i]=(a[i]+b[i]+c[i])/2 \qquad \text{Equation 9}$$

$$A[i]=(s[i](s[i]-a[i])\ (s[i]-b[i])(s[i]-c[i]))^{1/2} \qquad \text{Equation 10}$$

$$\text{Equation 11: } TA = \sum_{i=1}^{n} A[i]$$

wherein,
i: an element number (1 to the maximum element number)
a[i]: the length 1 of a side forming the element
b[i]: the length 2 of a side forming the element
c[i]: the length 3 of a side forming the element
s[i]: ½ of the sum of the lengths of the sides
A[i]: the area of each element
TA: a total area The area of each boundary surface can also be measured by multiplying the areas of the elements for each label number defined on the boundary surface in the equation 11. The total area of the boundary surfaces can be measured by obtaining TA which is the total area of the elements.

Figure 26:
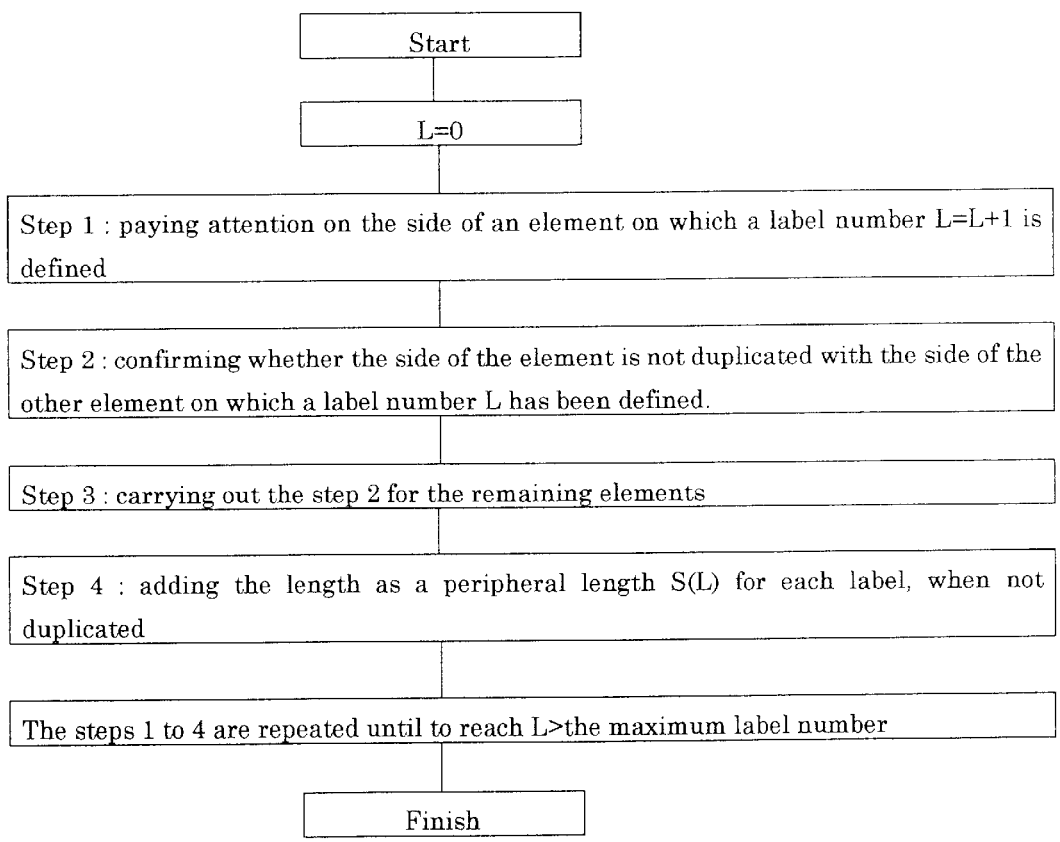
FIG. 26 is a flow chart for calculating a peripheral length.

Then, the peripheral length S of a boundary surface is measured by paying attention on a side coordinate formed from two nodes existing in an element-like state, confirming whether one or more sides having the same side coordinates exist in all other sides or not, paying attention on the next side after the first processing, applying the processing to the next side and then repeating the processing for all the other sides. Concretely, the peripheral length of the boundary surface is computed along the flow of FIG. 26. First, attention is paid on a side coordinate on an element having a defined label number L at the step 1 of FIG. 26. The side coordinate is the coordinates (X, Y, Z) of two nodes forming the side. Whether the attention-paid side having the label number L is duplicated with the sides of other elements or not is then confirmed at the step 2 of FIG. 26. The processing is applied to the remaining elements at the step 3. When not duplicated with the other side at the steps of FIG. 26, the side is the outermost peripheral side of the element having the label number L. The measured outermost peripheries of the sides are then multiplied for each label number to obtain the peripheral length S at the step 4 of FIG. 26. Finally, when the processing at the step 1 of FIG. 26 to the processing at the step 4 repeated at the step 5 of FIG. 26 are repeated, the peripheral length S (L) can be obtained for each label number.

The circular degree φ of the boundary surface is measured from the measured surface A and peripheral length S of the boundary surface by the next equation 12 for each label number of the boundary surface.

$$\phi[i]=4\pi A[i]/S[i]^2 \qquad \text{Equation 12}$$

wherein
- i: a label number (1 to the label number of the boundary surfaces)
- φ[i]: the circular degree of the boundary surface
- π[i]: pi
- A[i]: the area of the boundary surface
- S[i]: the peripheral length of the boundary surface The circular degree is 1.0, when the boundary surface is a perfect circle, and is decreased (a value near to 0) with the increase in the complexity of the shape. The circular degree of the boundary surface is computed by substituting the area A of the boundary surface and the peripheral length S of the boundary surface into the equation for each boundary surface. The average value of the computed circular degrees is measured as an average circular degree. Therein, the area A and peripheral length S of the explained boundary surface are used as the area A of the boundary surface and the peripheral length S of the boundary surface.

Tables 1 shows the measurement results of label numbers, total areas, total peripheral lengths, average circular degrees, and total areas/label numbers which are parameters related to the connected shapes of rat lumbar vertebra (10 pairs), and Tables 2 shows those of rat femur. The total area/label number is a value obtained by dividing the total area by the label number, namely shows an average area per independent unit boundary surface. When the correlation of the measured values with a bone strength index is examined, the bone strength can quantitatively be evaluated.

TABLE 1

| Sample | Label number | Total area | Total peripheral length | Average circular degree | Total area/label number |
|---|---|---|---|---|---|
| A | 864 | 9.126 | 318.677 | 0.584 | 0.011 |
| B | 844 | 11.181 | 355.802 | 0.573 | 0.013 |
| C | 1232 | 9.197 | 392.582 | 0.590 | 0.007 |
| D | 1030 | 11.376 | 362.472 | 0.587 | 0.011 |
| E | 892 | 12.151 | 361.669 | 0.582 | 0.014 |
| F | 1391 | 13.924 | 509.872 | 0.601 | 0.010 |
| G | 920 | 18.092 | 457.821 | 0.596 | 0.020 |
| H | 1126 | 23.227 | 611.263 | 0.583 | 0.021 |
| I | 969 | 7.546 | 301.585 | 0.580 | 0.008 |
| J | 978 | 11.700 | 388.046 | 0.586 | 0.012 | unit:area mm$^2$
unit:peripheral length mm

TABLE 2

| Sample | Label number | Total area | Total peripheral length | Average circular degree | Total area/label number |
|---|---|---|---|---|---|
| Normal condition | 349 | 8.254 | 247.7883 | 0.531 | 0.024 |
| Pathogenic condition | 321 | 5.464 | 161.0884 | 0.562 | 0.017 |
| Pathogenic condition + Medicine administration | 302 | 12.220 | 301.9848 | 0.529 | 0.040 | unit:area mm$^2$
unit:peripheral length mm

Figure 27:
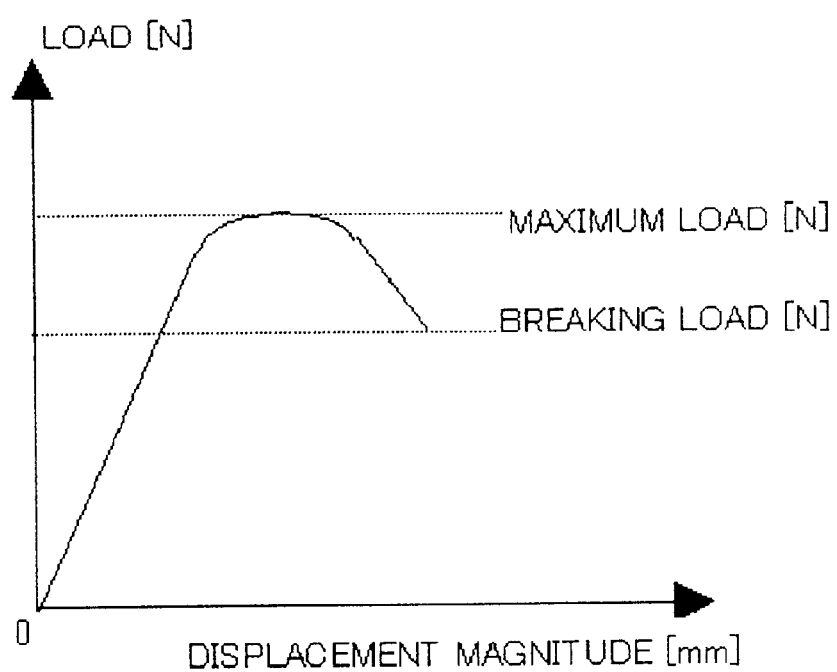
FIG. 27 is a flow chart for explaining indexes which reflect a bone strength.
Figure 28:
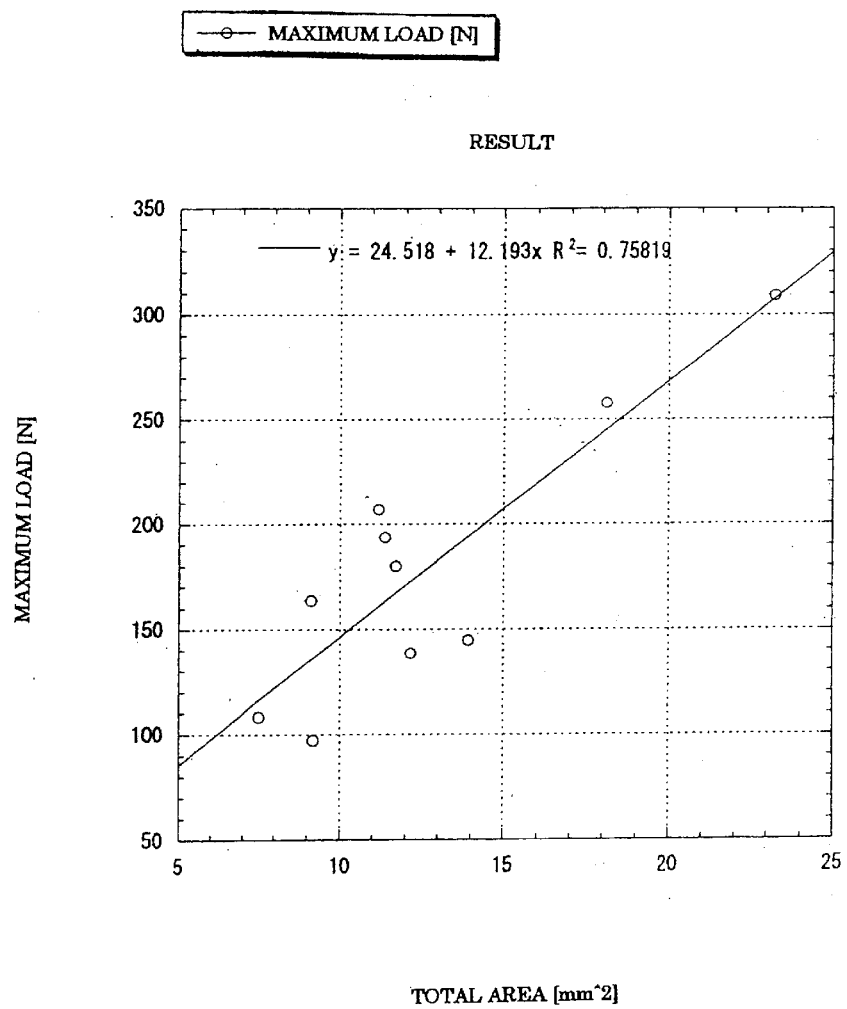
FIG. 28 is a correlation diagram of maximum load-total area.
Figure 29:
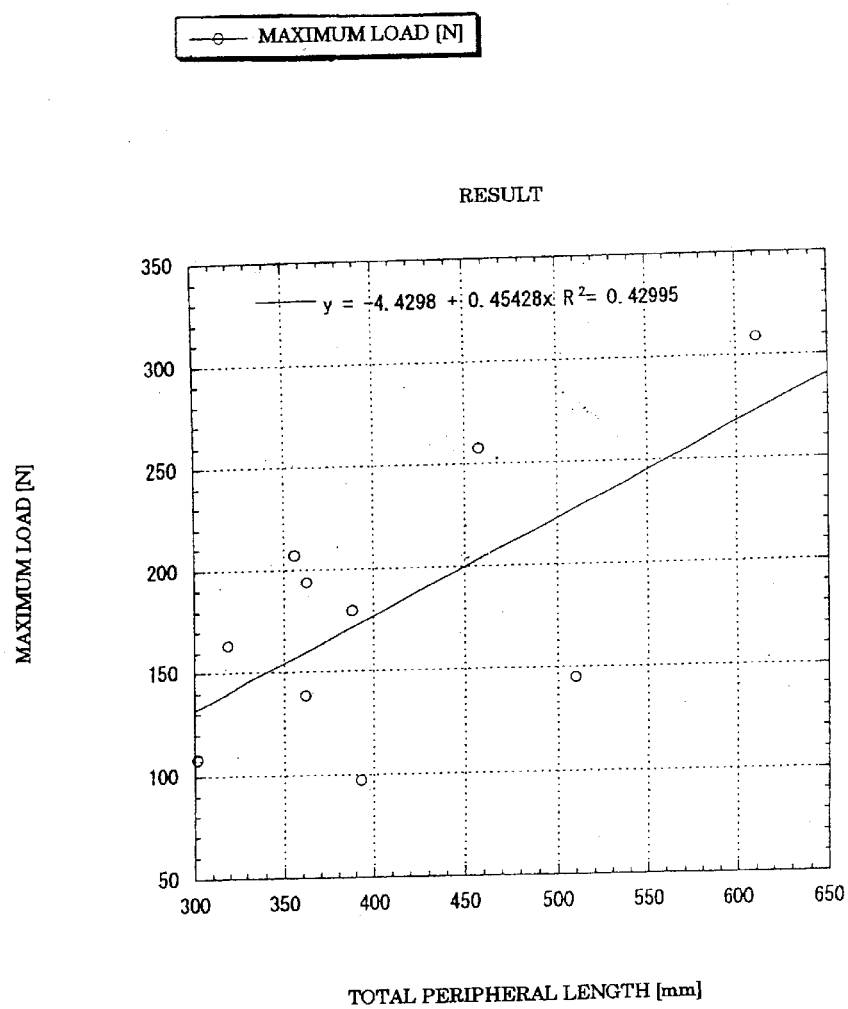
FIG. 29 is a correlation diagram of maximum load-total peripheral length.
Figure 30:
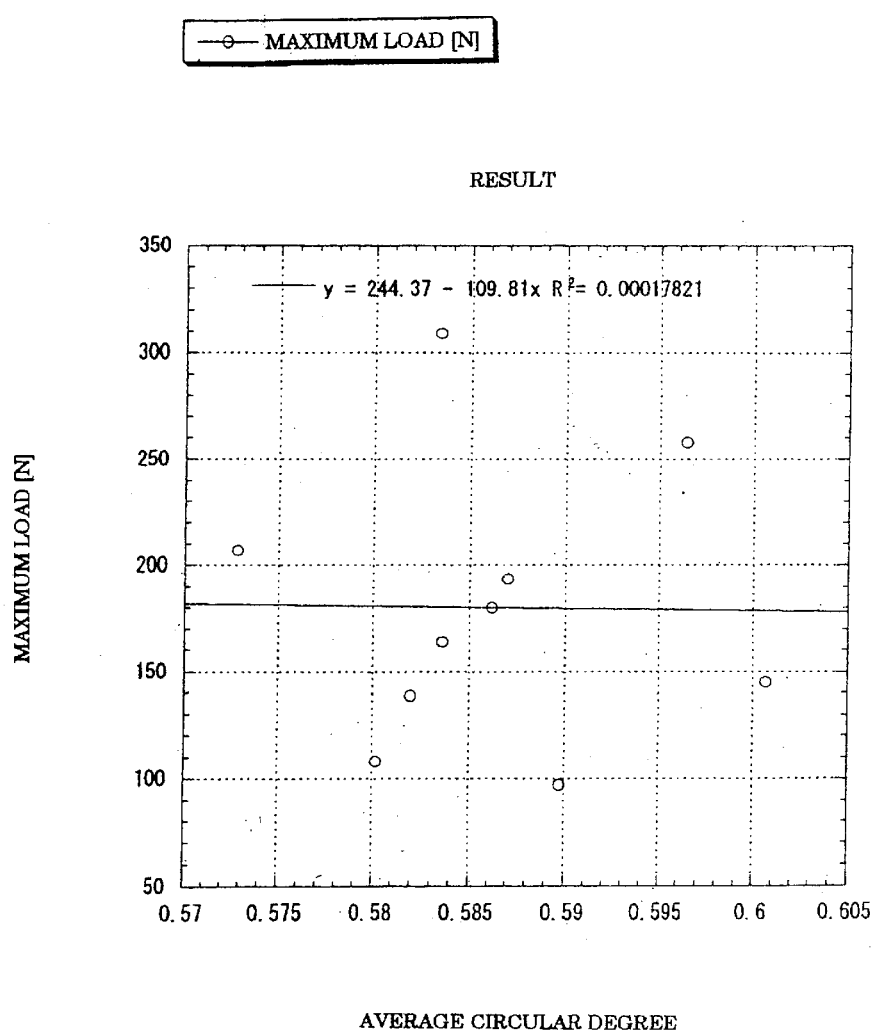
FIG. 30 is a correlation diagram of maximum load-average circular degree.
Figure 31:
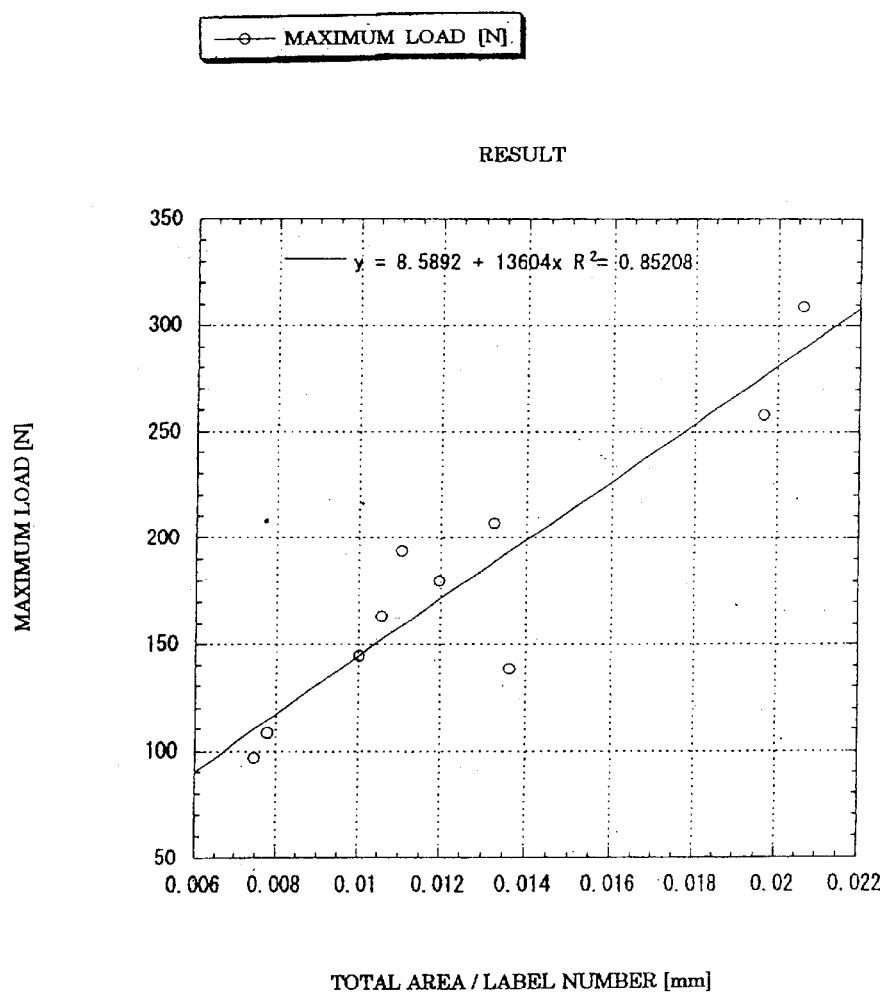
FIG. 31 is a correlation diagram of maximum load-total area/label number.

The bone strength index was evaluated using the maximum loads obtained by measuring the correlation of displacement magnitudes with applied loads as shown in FIG. 27. Table 3 shows the maximum loads of rat lumbar vertebras (10 pairs).

TABLE 3

| Sample | Maximum load [N] |
|---|---|
| A | 163.555 |
| B | 207.028 |
| C | 97.105 |
| D | 193.730 |
| E | 138.528 |
| F | 144.883 |
| G | 257.914 |
| H | 309.046 |
| I | 108.235 |
| J | 179.961 |

The correlations of the maximum loads with boundary characteristic parameters exhibited in Table 1 are shown in FIG. 28 to FIG. 31. Although the correlations of the maximum loads with the peripheral lengths and the average circular degrees could very largely not be recognized, the correlations of the maximum loads with the total areas and the total areas/label numbers were found to be high correlations of about $\gamma^2=0.76$ and about $\gamma^2=0.85$, respectively.

The method of the present invention can be used as software capable of being operated on various operation systems for computers, can be made using all computer languages, and can be built in any apparatus as software.

Effect of Invention

The method of the present invention enables the stable separation of the cortical bone portion and the cancellous bone portion by the simple processing, the non-invasive construction of the inner structure and architecture of the bone, and the high-speed, automatic and repeatable production of the three-dimensional information related to the cortical bone and the cancellous bone. Especially, the more accurate evaluation of the three-dimensional analysis of the bone than by conventional methods can be expected. In addition, the application of the processing method for estimating the surface shape of an orbit enables the simple and stable estimation of the boundary surface between the cortical bone portion and the cancellous bone portion topologically, the non-invasive visualization of the inner structure of the bone, and the repeatable quantification of the characteristics of the three-dimensional boundary surface between the cortical bone and the cancellous bone. In particular, the improved evaluation of the three-dimensional analysis of the bone can be expected. The method of the present invention can be applied not only to the lumbar vertebra but also to the femur, the so-called long bone. It can be expected that the present invention is applied to general image information that a diagnostic image obtained using the μX-ray CT, an X-ray film, a MRI or the like is a base for the three-dimensional evaluation of the bone. Further, the present invention can be applied to an evaluation method for evaluating the bone or joint of an animal model of bone-related disease or joint-related disease and to a clinical evaluation method for evaluating the bone or joint of a patient of bone-related disease or joint-related disease, whereby the application of the present invention to the development of a medicine or a therapeutic method by the use of animal models, and to clinical tests, daily diagnoses and treatments accurate diagnoses, and the judgment of the effects of a medicine and a therapeutic method can be expected.

What is claimed is:

1. A bone measurement method for separating a cortical bone and a cancellous bone on the basis of the binary image of a test bone cross section, characterized by having a template image extraction step for obtaining the wholly continued template image of a bone inner portion surrounded by the cortical bone from said binary image, and separating the cortical bone and the cancellous bone by the product of said template image and said binary image wherein a three-dimensional separated bone image is produced by forming separated images of a cortical bone portion and a cancellous bone portion from a plurality of continuous tomographic images obtained from a test bone at a prescribed distance and then stacking the separated images.

2. A bone measurement method described in claim 1 characterized in that a template image extraction step comprises a hole-filling step for filling the hole portions of said inner bone portion of said binary image to obtain a wholly continued inner bone portion image, an image subtraction step for subtracting said binary image from the filled inner bone portion image, and a deletion step for deleting the spaces of the image obtained at the image subtraction step to obtain a template image.

3. A bone measurement method described in claim 2 characterized in that a hole-filling step comprises an expansion step for carrying out expansion processing prescribed times to delete the images of a cancellous bone portion and so on, an inversion step for inverting at least the inner bone image portion of the expanded image after expansion, an image addition step for adding the inverted image to the expanded image to obtain a wholly continued inner bone portion image, and a shrinkage step for shrinking the added image prescribed times to shrink the size of the added image to the size of the original image.

4. A bone measurement method described in claim 2 characterized in that a deletion step is a step for expanding an image prescribed times and then shrinking the expanded image prescribed times.

5. A bone measurement method described in claim 1 characterized in that a separated image separated into a cortical bone and a cancellous bone is converted into a separated image of gray-values by the product of the obtained binary separated image and the non-binary gray-scale image.

6. A method for processing an image, characterized in that a cut separated surface portion (hereinafter referred to as "boundary surface") between a cortical bone and a cancellous bone is defined by applying a method for defining the boundary surface of an object to the boundary surface on the image separated into a cortical bone and the cancellous bone on the basis of the binary image of the test bone cross section, wherein a three-dimensional separated bone image is produced by forming separated images of a cortical bone portion and a cancellous bone portion from a plurality of continuous tomographic images obtained from a test bone at a prescribed distance and then stacking the separated images, and wherein said three-dimensional separated bone image defines boundary surfaces.

7. A bone measurement method for obtaining information related to the number of independent boundary surfaces in a three-dimensional space by labeling the components of boundary surfaces, with respect to the boundary surfaces produced by the image-processing method of claim 6.

8. A measurement method for obtaining information related to the areas of independent boundary surfaces in a three-dimensional space, with respect to the boundary surfaces produced by the image-processing method of claim 6.

9. A measurement method for obtaining information related to the peripheral lengths of independent boundary surfaces in a three-dimensional space, with respect to the boundary surfaces produced by the image-processing method of claim 6.

10. A measurement method for obtaining information related to the circular degrees of independent boundary surfaces in a three-dimensional space, with respect to the boundary surfaces produced by the image-processing method of claim 6.

11. A clinical evaluation method for evaluating a bone and a joint in an animal model of bone-related disease or joint-related disease, by using the bone measurement method of claim 1.

12. An evaluation method for evaluating a bone and a joint in a patient of bone-related disease or joint-related disease, by using the bone measurement method of claim 1.

* * * * *